(12) United States Patent
Hashimoto et al.

(10) Patent No.: US 9,983,144 B2
(45) Date of Patent: May 29, 2018

(54) PLASMA LIGHT SOURCE AND INSPECTION APPARATUS INCLUDING THE SAME

(71) Applicants: Kohei Hashimoto, Suwon-si (KR);
Nobuyuki Kimura, Yokohama (JP);
Wook-rae Kim, Suwon-si (KR);
Byeong-hwan Jeon, Yongin-si (KR)

(72) Inventors: Kohei Hashimoto, Suwon-si (KR);
Nobuyuki Kimura, Yokohama (JP);
Wook-rae Kim, Suwon-si (KR);
Byeong-hwan Jeon, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 81 days.

(21) Appl. No.: 14/964,065

(22) Filed: Dec. 9, 2015

(65) Prior Publication Data
US 2016/0169814 A1    Jun. 16, 2016

(30) Foreign Application Priority Data
Dec. 11, 2014   (KR) .................. 10-2014-0178713

(51) Int. Cl.
*H01J 61/62* (2006.01)
*H05G 2/00* (2006.01)
(Continued)

(52) U.S. Cl.
CPC ..... *G01N 21/8806* (2013.01); *G01N 21/9501* (2013.01); *G01N 21/956* (2013.01); *G02B 21/06* (2013.01); *G02B 27/141* (2013.01); *G03F 7/70616* (2013.01); *H01J 61/025* (2013.01); *H01J 65/04* (2013.01); *H05G 2/008* (2013.01)

(58) Field of Classification Search
CPC .......... G01N 21/8806; G01N 21/9501; G01N 21/956; G02B 21/06; G02B 27/141; G03F 7/2004; H01J 65/04; H01J 65/11
See application file for complete search history.

(56) References Cited

U.S. PATENT DOCUMENTS 6,265,813 B1   7/2001   Knox et al.
7,368,741 B2   5/2008   Melnychuk et al.
(Continued)

FOREIGN PATENT DOCUMENTS

JP    2010-171219      8/2010
JP    2010-210717      9/2010
KR    1020130076982    7/2013

*Primary Examiner* — Eliza Osenbaugh-Stewart
(74) *Attorney, Agent, or Firm* — Myers Bigel, P.A.

(57) ABSTRACT

Provided are a plasma light source capable of solving a problem occurring when an arc discharge lamp is used and an inspection apparatus capable of providing uniform and high-brightness plasma light. The plasma light source includes a pulse laser generator configured to generate a pulse laser beam, a continuous wave (CW) laser generator configured to generate an infrared ray (IR) CW laser beam, a first dichroic mirror configured to transmit or reflect the pulse laser beam and reflect or transmit the IR CW laser beam, a chamber configured to receive the pulse laser beam to ignite plasma and the IR CW laser beam to maintain the plasma in an ignited state, and discharge plasma light generated by the plasma, and a second dichroic mirror configured to transmit the pulse laser beam and the IR CW laser beam and reflect the plasma light.

14 Claims, 25 Drawing Sheets

(51) Int. Cl.
*G01N 21/88* (2006.01)
*G02B 27/14* (2006.01)
*G02B 21/06* (2006.01)
*G01N 21/95* (2006.01)
*G01N 21/956* (2006.01)
*G03F 7/20* (2006.01)
*H01J 61/02* (2006.01)
*H01J 65/04* (2006.01)

(56) References Cited

U.S. PATENT DOCUMENTS

| | | |
|---|---|---|
| 7,385,212 B2 | 6/2008 | Murakami |
| 7,435,982 B2 | 10/2008 | Smith |
| 7,654,715 B1 * | 2/2010 | Chen ................. G01N 21/8806 359/368 |
| 7,786,455 B2 | 8/2010 | Smith |
| 7,989,786 B2 | 8/2011 | Smith et al. |
| 8,242,695 B2 | 8/2012 | Sumitomo et al. |
| 8,369,374 B2 | 2/2013 | Yokota |
| 8,431,916 B2 | 4/2013 | Loopstra et al. |
| 8,651,701 B2 * | 2/2014 | Yasuda ................. H01J 61/025 250/493.1 |
| 8,841,824 B2 | 9/2014 | Ko et al. |
| 2002/0094685 A1 * | 7/2002 | Nakata ................... G01N 21/53 438/689 |
| 2007/0058375 A1 * | 3/2007 | Wang .................... F21V 7/0025 362/341 |
| 2007/0206184 A1 * | 9/2007 | Uto ........................ G01N 21/21 356/237.2 |
| 2007/0228300 A1 * | 10/2007 | Smith .................... B82Y 10/00 250/504 R |
| 2010/0164347 A1 * | 7/2010 | Yasuda ................. H01J 61/025 313/46 |
| 2011/0032711 A1 | 2/2011 | Baacke et al. |
| 2012/0161631 A1 | 6/2012 | Kuwabara |
| 2013/0105712 A1 * | 5/2013 | Yanagida ............... H05G 2/003 250/504 R |
| 2013/0169140 A1 | 7/2013 | Ko et al. |
| 2013/0175921 A1 | 7/2013 | Espiau et al. |
| 2013/0207004 A1 | 8/2013 | Ceglio et al. |
| 2014/0042336 A1 * | 2/2014 | Bezel ....................... H01J 61/02 250/424 |
| 2014/0375987 A1 * | 12/2014 | Brunner ............. G01N 21/8806 356/237.5 |

* cited by examiner

FIG. 12A
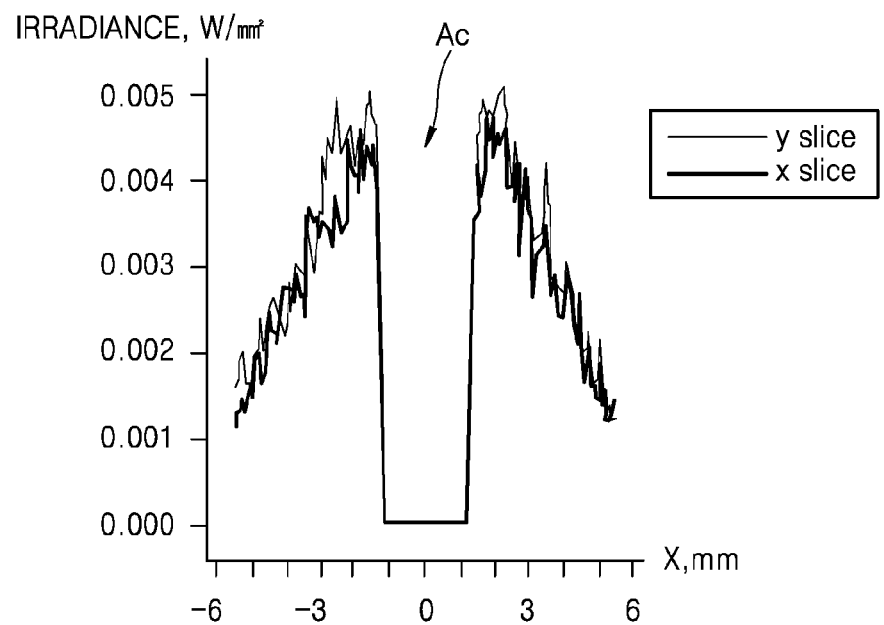
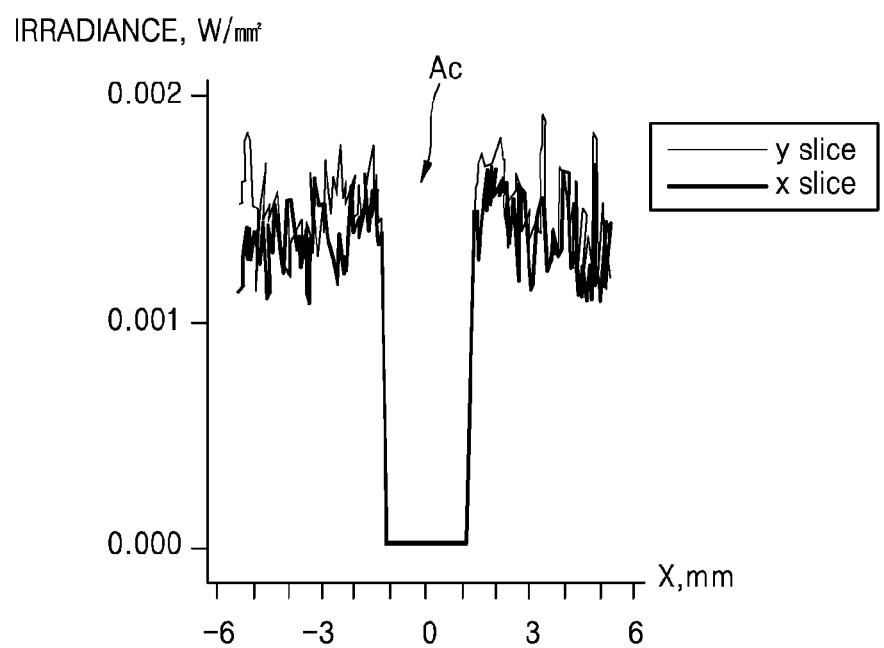
FIG 12B

FIG. 20A
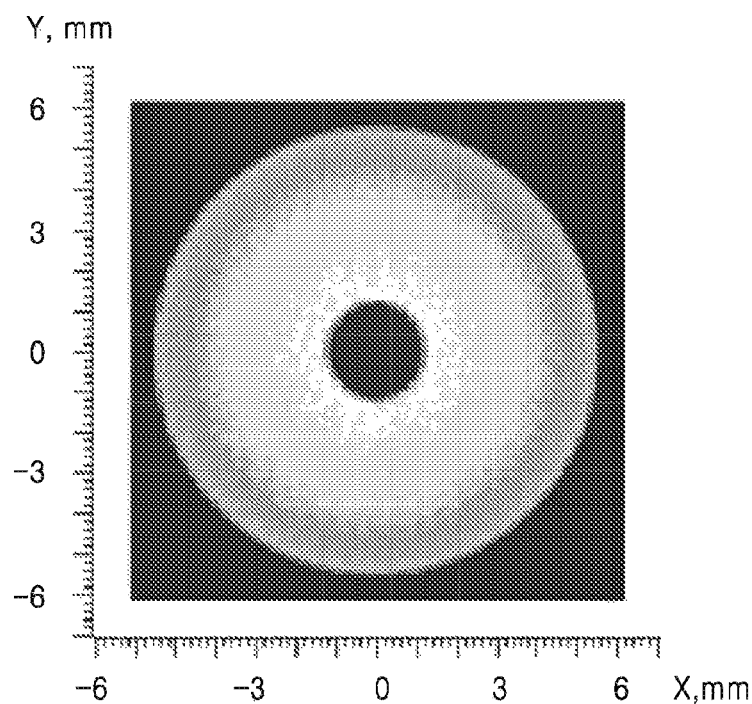
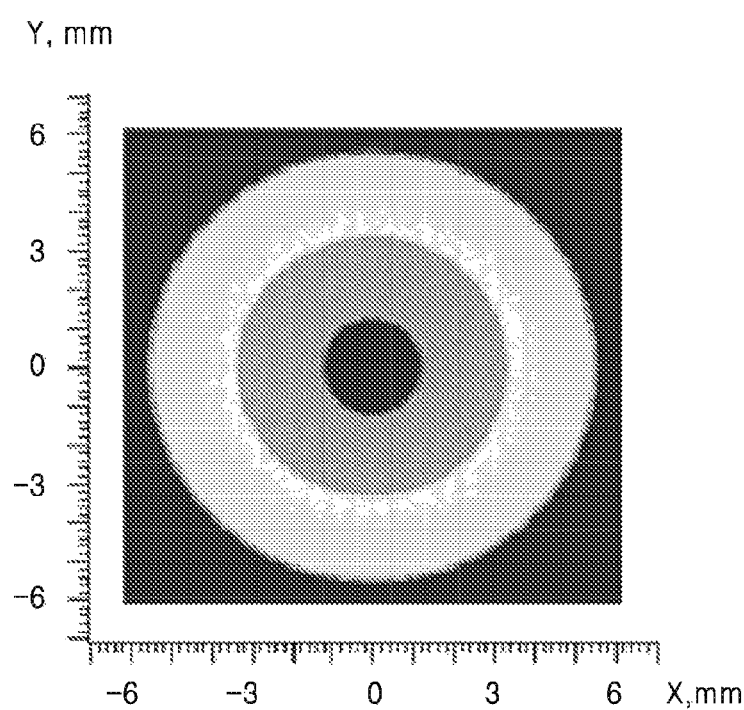
FIG. 20B

FIG. 21A
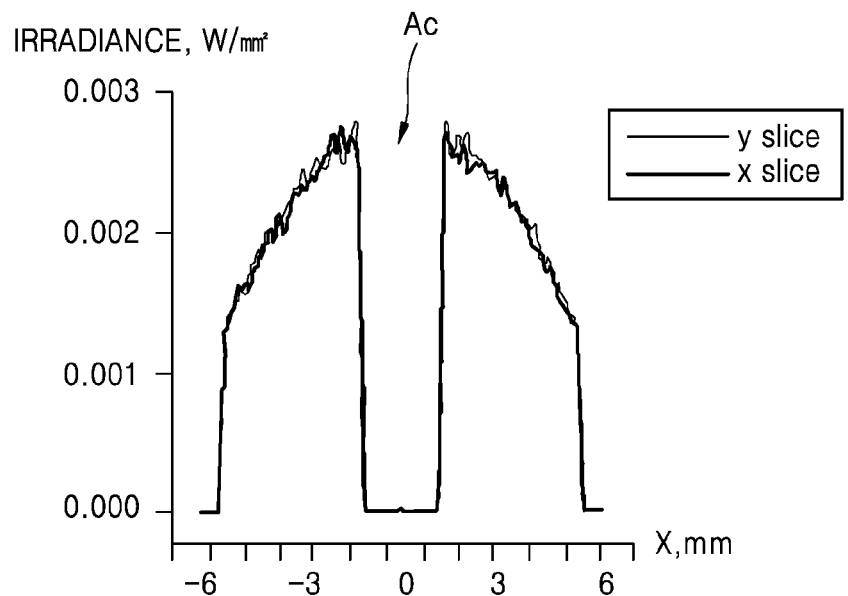
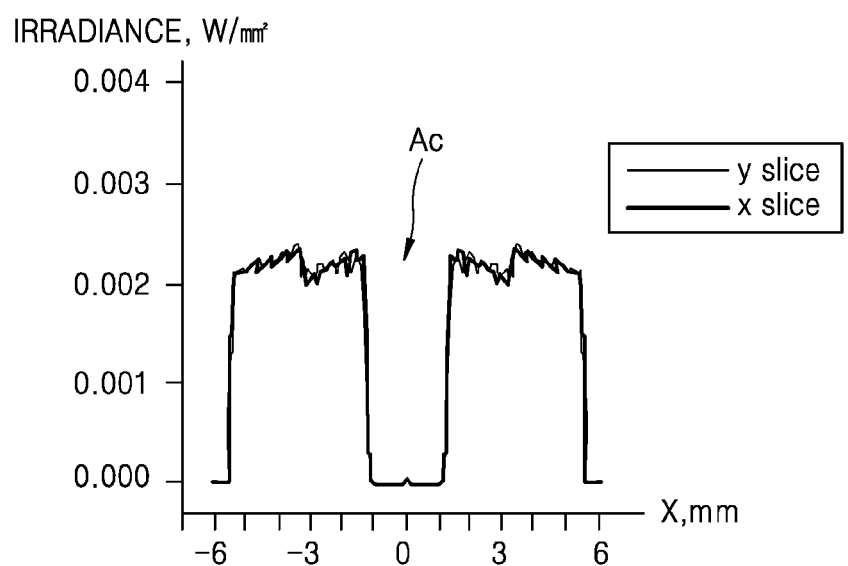
FIG. 21B

PLASMA LIGHT SOURCE AND INSPECTION APPARATUS INCLUDING THE SAME

CROSS-REFERENCE TO RELATED APPLICATION

This application claims priority to Korean Patent Application No. 10-2014-0178713, filed on Dec. 11, 2014, the disclosure of which is incorporated by reference herein in its entirety.

BACKGROUND

The inventive concept relates to a light source and an inspection apparatus, and more particularly, to a plasma light source for use in a semiconductor manufacturing process or an inspection process, and an inspection apparatus capable of providing high-brightness plasma light.

High-brightness light sources may be used in various applications. For example, the high-brightness light sources may be used to examine, test, or measure characteristics of semiconductor wafers or materials used in manufacturing semiconductor wafers. In addition, electromagnetic energy, which is produced by the high-brightness light source, may be used in a lithography system, a microscopy system, or a photoresist curing system, which is used in manufacturing wafers. On the other hand, parameters of light, such as a wavelength, a power level, and brightness, may be different depending on the fields of applications. Specifically, for example, a wafer inspection system supplies light by using xenon or mercury arc lamps. The arc lamps may include a positive electrode and a negative electrode for exciting xenon or mercury gas within a lamp. When the arc lamp generates light, the positive electrode and the negative electrode may be worn out, or contaminant particles may be generated. Furthermore, in some fields, in particular, in the fields of ultraviolet spectrum, satisfactory brightness may not be provided.

SUMMARY

The inventive concept provides a plasma light source capable of solving a problem occurring when an arc discharge lamp is used, and an inspection apparatus capable of providing uniform and high-brightness plasma light.

According to an aspect of the inventive concept, there is provided a plasma light source including a pulse laser generator configured to generate a pulse laser beam, a continuous wave (CW) laser generator configured to generate an infrared ray (IR) CW laser beam, a first dichroic mirror configured to transmit or reflect the pulse laser beam and reflect or transmit the IR CW laser beam, a chamber configured to receive the pulse laser beam to ignite plasma and the IR CW laser beam to maintain the plasma in an ignited state, and to discharge plasma light generated by the plasma, and a second dichroic mirror configured to transmit the pulse laser beam and the IR CW laser beam and reflect the plasma light.

In some embodiments, the chamber has no electrodes therein.

In some embodiments, the chamber is surrounded by an elliptical mirror and is disposed at a focus of the elliptical mirror, and the pulse laser beam and the IR CW laser beam are concentrated on the chamber by the elliptical mirror.

In some embodiments, the first dichroic mirror and the second dichroic mirror are disposed on a same axis to selectively reflect or transmit light according to a wavelength, so that input light beams incident on the chamber are synthesized and an output light beam from the chamber is separated from the input light beams.

In some embodiments, the pulse laser beam is input to the chamber by reflection of the first dichroic mirror and transmission of the second dichroic mirror, and the IR CW laser beam passes through the first dichroic mirror and the second dichroic mirror and is input to the chamber. In some embodiments, a concave lens is disposed between the pulse laser generator and the first dichroic mirror, and a cylindrical lens is disposed between the CW laser generator and the first dichroic mirror.

In some embodiments, the pulse laser beam and the IR CW laser beam are ring-shaped beams and are input to the first dichroic mirror. In some embodiments, the ring-shaped beams are formed using a pair of axicon lenses or a spatial light modulator (SLM).

According to another aspect of the inventive concept, there is provided a plasma light source including a first dichroic mirror configured to transmit or reflect a pulse laser beam and reflect or transmit an infrared ray (IR_ continuous wave (CW) laser beam, a chamber configured to receive the pulse laser beam to ignite plasma and the IR CW laser beam to maintain the plasma in an ignited state, and discharge plasma light generated by the plasma, a second dichroic mirror configured to transmit or reflect the pulse laser beam and the IR CW laser beam and to reflect the plasma light, and a reflection structure including a combination of an elliptical mirror and a spherical mirror and configured to homogenize the plasma light in terms of angle by reflection of the elliptical mirror and the spherical mirror so that the plasma light is directed in one direction.

In some embodiments, the pulse laser beam and the IR CW laser beam are ring-shaped beams and are input to the first dichroic mirror.

In some embodiments, the pulse laser beam is input to the chamber by reflection of the first dichroic mirror and transmission of the second dichroic mirror, the IR CW laser beam passes through the first dichroic mirror and the second dichroic mirror and is input to the chamber, and the plasma light is output by reflection of the second dichroic mirror.

In some embodiments, the elliptical mirror has a structure that is opened in one direction, the spherical mirror is opened in a first direction and a second direction, the first direction being directed toward the elliptical mirror and the second direction being directed toward the one direction, and the reflection structure is configured such that an opened portion of the spherical mirror in the first direction is coupled to an opened portion of the elliptical mirror. In some embodiments, the spherical mirror reflects the plasma light, which is not reflected by the elliptical mirror, toward the elliptical mirror. In some embodiments, a diameter of the opened portion of the spherical mirror in the first direction is greater than a diameter of the opened portion of the spherical mirror in the second direction, the diameter of the opened portion of the spherical mirror in the first direction is greater than a diameter of the opened portion of the elliptical mirror, and the opened portion of the spherical mirror in the second direction has a sufficient diameter to transmit the plasma light reflected by the elliptical mirror without being blocked. In some embodiments, the spherical mirror is configured to homogenize the intensity of the plasma light in a central area and the intensity of the plasma light in an outer peripheral area on a cross section perpendicular to a traveling direction of the plasma light. In some embodiments, the central area is an area where the plasma light is reflected by only the elliptical mirror, and the outer peripheral area is an area where the plasma light is reflected by the elliptical mirror and the spherical mirror. In some embodiments, the elliptical mirror and the spherical mirror have a same focus, and the chamber is disposed at the same focus of the elliptical mirror and the spherical mirror.

According to another aspect of the inventive concept, there is provided an inspection apparatus including: a plasma light source including a first dichroic mirror configured to transmit or reflect a pulse laser beam and to reflect or transmit an infrared ray (IR) continuous wave (CW) laser beam, a chamber configured to receive the pulse laser beam to ignite plasma and the IR CW laser beam to maintain the plasma in an ignited state, and discharge plasma light generated by the plasma, and a second dichroic mirror configured to transmit or reflect the pulse laser beam and the IR CW laser beam and reflect the plasma light, a homogenizer configured to receive the plasma light and spatially homogenize the plasma light, a uniformizing device configured to make the plasma light uniform in terms of angle and input the uniform plasma light to the homogenizer, a first optical system configured to transfer light output from the homogenizer to an inspection object, and an optical detector configured to detect light reflected from the inspection object.

In some embodiments, the chamber is surrounded by an elliptical mirror and is disposed at a focus of the elliptical mirror, the pulse laser beam and the IR CW laser beam are concentrated on the chamber by the elliptical mirror, and the first dichroic mirror and the second dichroic mirror reflect or transmit light according to a wavelength, so that input light beams incident on the chamber are synthesized and an output light beam from the chamber is separated from the input light beams.

In some embodiments, the chamber has no electrodes therein.

In some embodiments, the uniformizing device includes a neutral density (ND) filter disposed between the plasma light source and the homogenizer and configured to gradually reduce the transmittance of the plasma light toward a central area of a cross section perpendicular to a traveling direction of the plasma light.

In some embodiments, the uniformizing device is a reflection structure that includes a combination of an elliptical mirror and a spherical mirror and reflects the plasma light in one direction, the elliptical mirror has a structure that is opened in a direction of the homogenizer, the spherical mirror is opened in a first direction and a second direction, the first direction being directed toward the elliptical mirror and the second direction being directed toward the homogenizer, and the reflection structure is configured such that an opened portion of the spherical mirror in the first direction is coupled to an opened portion of the elliptical mirror.

In some embodiments, the spherical mirror is configured to reflect the plasma light, which is not reflected by the elliptical mirror, toward the elliptical mirror, and the spherical mirror is configured to homogenize the intensity of the plasma light in a central area and the intensity of the plasma light in an outer peripheral area on a cross section perpendicular to a traveling direction of the plasma light.

In some embodiments, the uniformizing device includes: a reflection structure that includes a combination of an elliptical mirror and a spherical mirror and reflects the plasma light in one direction; and a neutral density (ND) filter disposed between the reflection structure and the homogenizer and configured to gradually reduce the transmittance of the plasma light toward a central area of a cross section perpendicular to a traveling direction of the plasma light.

In some embodiments, the first optical system includes: a collimation lens configured to collimate light output from the homogenizer into parallel light; and an objective lens configured to irradiate the parallel light on the inspection object and receive light reflected from the inspection object, and the inspection apparatus further comprises a beam splitter disposed between the collimation lens and the objective lens or between the homogenizer and the collimation lens to split the light irradiated on the inspection object and the light reflected from the inspection object.

According to some embodiments of the inventive concept, an inspection apparatus includes a plasma light source including a first dichroic mirror configured to transmit or reflect a pulse laser beam and reflect or transmit an infrared ray (IR) continuous wave (CW) laser beam; a chamber configured to receive the pulse laser beam to ignite plasma and the IR CW laser beam to maintain the plasma in an ignited state, and discharge plasma light generated by the plasma; and a second dichroic mirror configured to transmit or reflect the pulse laser beam and the IR CW laser beam and reflect the plasma light; a first optical system configured to transfer plasma light to an inspection object; and a second optical system comprising an optical detector configured to detect light reflected from the inspection object.

In some embodiments, the chamber is surrounded by an elliptical mirror and is disposed at a focus of the elliptical mirror, the pulse laser beam and the IR CW laser beam are concentrated on the chamber by the elliptical mirror, and the first dichroic mirror and the second dichroic mirror reflect or transmit light according to a wavelength, so that input light beams incident on the chamber are synthesized and an output light beam from the chamber is separated from the input light beams.

In some embodiments, the chamber has no electrodes therein.

In some embodiments, the inspection apparatus further includes a uniformizing device including a neutral density (ND) filter disposed between the plasma light source and the first optical system and configured to gradually reduce the transmittance of the plasma light toward a central area of a cross section perpendicular to a traveling direction of the plasma light. In some embodiments, the uniformizing device is a reflection structure that includes a combination of an elliptical mirror and a spherical mirror and reflects the plasma light in one direction, the elliptical mirror has a structure that is opened in a direction of the homogenizer, the spherical mirror is opened in a first direction and a second direction, the first direction being directed toward the elliptical mirror and the second direction being directed toward the homogenizer, and the reflection structure is configured such that an opened portion of the spherical mirror in the first direction is coupled to an opened portion of the elliptical mirror. In some embodiments, the spherical mirror is configured to reflect the plasma light, which is not reflected by the elliptical mirror, toward the elliptical mirror, and the spherical mirror is configured to homogenize the intensity of the plasma light in a central area and the intensity of the plasma light in an outer peripheral area on a cross section perpendicular to a traveling direction of the plasma light.

In some embodiments, the inspection apparatus further includes a uniformizing device including a reflection structure that includes a combination of an elliptical mirror and a spherical mirror and reflects the plasma light in one direction; and a neutral density (ND) filter disposed between the reflection structure and the first optical system and configured to gradually reduce the transmittance of the plasma light toward a central area of a cross section perpendicular to a traveling direction of the plasma light. In some embodiments, the first optical system includes: a collimation lens configured to collimate light output from the homogenizer into parallel light; and an objective lens configured to irradiate the parallel light on the inspection object and receive light reflected from the inspection object, and the inspection apparatus further comprises a beam splitter disposed between the collimation lens and the objective lens or between the homogenizer and the collimation lens to split the light irradiated on the inspection object and the light reflected from the inspection object.

BRIEF DESCRIPTION OF THE DRAWINGS

Example embodiments of the inventive concept will be more clearly understood from the following detailed description taken in conjunction with the accompanying drawings in which:

FIGS. 12A and 12B are graphs of the light intensity distributions in an x slice and a y slice correspond to the images of FIGS. 11A and 11B, respectively;

FIG. 20A is a simulation image of a light intensity distribution when only an elliptical mirror is present in the inspection apparatus of FIG. 16, and FIG. 20B is a simulation image of a light intensity distribution when a reflection structure including a spherical mirror is present in the inspection apparatus of FIG. 16;

FIGS. 21A and 21B are graphs of light intensity distributions in an x slice and a y slice corresponding to the images of FIGS. 20A and 20B, respectively.

DETAILED DESCRIPTION OF THE EMBODIMENTS

Figure 1A:
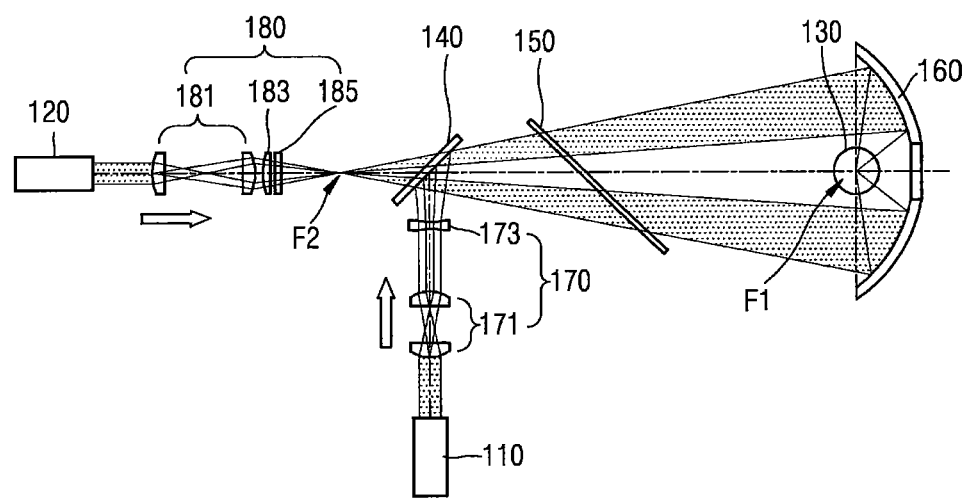
FIGS. 1A and 1B are schematic diagrams of a plasma light source according to example embodiments of the inventive concept.

Hereinafter, example embodiments of the inventive concept will be described with reference to the accompanying drawings. The inventive concept may, however, be embodied in many different forms and should not be construed as being limited to the example embodiments set forth herein; rather, these example embodiments are provided so that this disclosure will be thorough and complete, and will fully convey the inventive concept to those of ordinary skill in the art. As used herein, the term "and/or" includes any and all combinations of one or more of the associated listed items.

It will be understood that when an element, such as a layer, a region, or a substrate, is referred to as being "on" or "connected to" another element, it may be directly on, connected or coupled to the other element or intervening elements may be present. In the drawings, the dimensions of structures are exaggerated for clarity of the inventive concept. Parts having no relation to the description are omitted. Like reference numerals denote like elements throughout the specification and drawings. The terminology used herein is for the purpose of describing particular example embodiments only and is not intended to be limiting of the inventive concept.

Figure 1B:
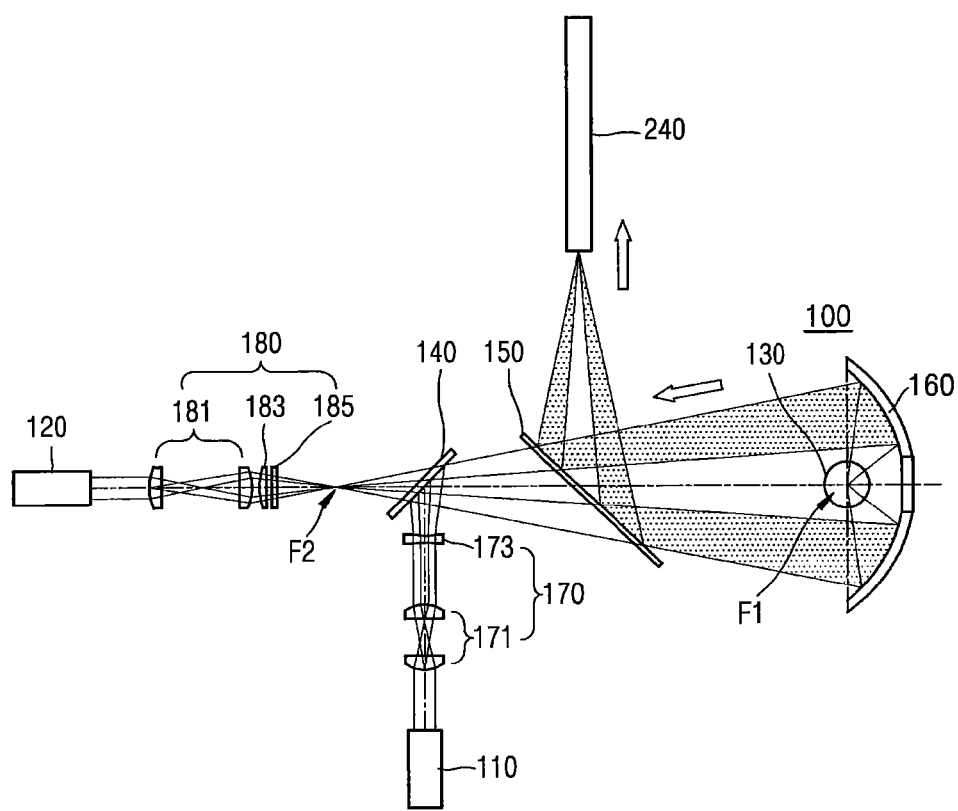
Figure 2:
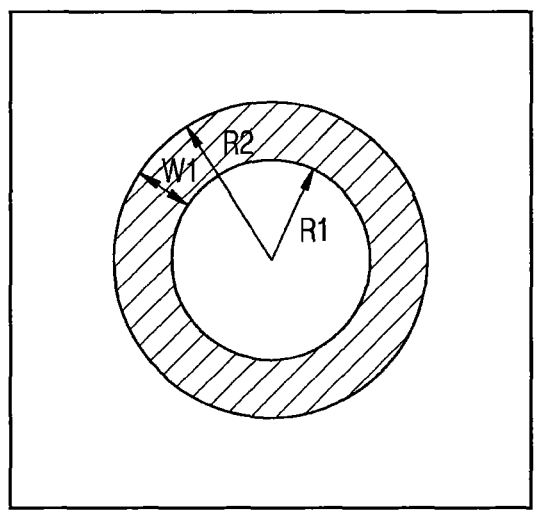
FIG. 2 is a schematic diagram illustrating light passing through a pair of axicon lenses in the plasma light source of FIG. 1A.

FIGS. 1A and 1B are schematic diagrams of a plasma light source 100 according to an example embodiment of the inventive concept. FIG. 1A illustrates a process of inputting an infrared ray continuous wave (CW) laser beam and a pulse laser beam to a chamber 130, and FIG. 1B illustrates a process of outputting plasma light from the chamber 130. FIG. 2 is a schematic diagram of light passing through a pair of axicon lenses in the plasma light source 100 of FIGS. 1A and 1B.

Referring to FIGS. 1A and 1B, the plasma light source 100 according to example embodiments may include a pulse laser generator 110, a CW laser generator 120, the chamber 130, first and second dichroic mirrors 140 and 150, and an elliptical mirror 160. In addition, the plasma light source 100 may further include a first input optical system 170 configured to input a pulse laser beam to the first dichroic mirror 140, and a second input optical system 180 configured to input a CW laser beam to the second dichroic mirror 150.

The pulse laser generator 110 may generate a pulse laser beam, for example, a visible ray pulse laser beam, and input the pulse laser beam to the chamber 130. The pulse laser beam, which is generated by the pulse laser generator 110, is not limited to a visible ray pulse laser beam. For example, the pulse laser beam, which is generated by the pulse laser generator 110, may have various wavelengths, such as infrared rays or ultraviolet rays.

On the other hand, the pulse laser beam, which is generated by the pulse laser generator 110, may have very high peak power. For example, the pulse laser beam may have sufficient peak power to ignite plasma in the chamber 130. In addition, since the pulse laser beam is used only for plasma ignition, the time taken to input the pulse laser beam to the chamber 130 may be short and the average power of the pulse laser beam may be low. Therefore, light emission of the plasma ignited by the pulse laser beam may be weak.

During a predetermined period of time after the plasma ignition, the pulse laser beam may be continuously input to the chamber 130.

The pulse laser beam may be converted into a ring-shaped beam through the first input optical system 170 and be input to the elliptical mirror 160 by the reflection of the first dichroic mirror 140 and the transmission of the second dichroic mirror 150. Since the pulse laser beam is input to the chamber 130 by the reflection of the elliptical mirror 160 and is concentrated, the pulse laser beam is capable of igniting plasma. The configurations and functions of the first dichroic mirror 140, the second dichroic mirror 150, and the elliptical mirror 160 are described below in more detail.

The CW laser generator 120 may generate a CW laser beam, for example, an infrared ray (IR) CW laser beam, and input the CW laser beam to the chamber 130. The CW laser beam, which is generated by the CW laser generator 120, is not limited to an IR CW laser beam.

The CW laser beam, which is generated by the CW laser generator 120, may be input to the chamber 130 so as to maintain the plasma in an ignited state and to increase the ignited plasma to high power. Accordingly, the CW laser beam may be, for example, a high-power CW laser beam having sufficient energy to maintain the plasma in an ignited state and increase the intensity of plasma.

The CW laser beam may be converted into a ring-shaped beam through the second input optical system 180, pass through the first dichroic mirror 140 and the second dichroic mirror 150, and be input to the elliptical mirror 160. Since the CW laser beam is input to the chamber 130 by the reflection of the elliptical mirror 160 and is concentrated, the CW laser beam may contribute to maintaining the plasma in an ignited state and increasing the intensity of the plasma. On the other hand, the pulse laser beam and the CW laser beam are concentrated and superimposed at the same converging point, for example, a focus of the elliptical mirror 160, in the chamber 130 by the reflection of the elliptical mirror 160. Thus, high-power plasma may be generated. After the generation of the high-power plasma, the high-power plasma may be maintained even when the pulse laser beam is interrupted.

The pulse laser generator 110 and the CW laser generator 120 may include collimation lenses, respectively, so as to output the pulse laser beam and the CW laser beam as parallel light.

The chamber 130 or a lamp may accommodate a medium material for plasma ignition. That is, the chamber 130 may airtightly accommodate a medium material for plasma ignition in a solid, liquid, or gas state at an early stage. The medium material for plasma ignition may also be referred to as an ionizable medium material. The chamber 130 may be supported by a support (not illustrated) and be fixed to the elliptical mirror 160. For example, the chamber 130 may be supported by the support connected to a portion that does not contribute to the reflection of the elliptical mirror 160 and be fixed to the focus of the elliptical mirror 160. More specifically, the chamber 130 may be fixed to the elliptical mirror 160 such that the converging point in the chamber 130 matches the focus of the elliptical mirror 160.

The chamber 130 may be made of at least one selected from the group consisting of a dielectric material, a quartz material, suprasil quartz, sapphire, magnesium fluoride ($MgF_2$), diamond, and calcium fluoride ($CaF_2$). The material of the chamber 130 may be appropriately selected by taking into account the medium material for plasma ignition to be accommodated in the chamber 130 and/or plasma light at a wavelength to be generated and output by the chamber 130.

In the present example embodiment, the chamber 130 may be made of a material that is transparent to a pulse laser beam, a CW laser beam, and ultraviolet (UV) rays. Accordingly, the chamber 130 may discharge plasma light corresponding to the UV rays among the generated plasma light beams.

The chamber 130 may accommodate various medium materials for plasma ignition. For example, the medium material for plasma ignition may be at least one selected from the group consisting of a noble gas, xenon (Xe), argon (Ar), neon (Ne), krypton (Kr), helium (He), deuterium ($D_2$), hydrogen ($H_2$), oxygen ($O_2$), fluorine ($F_2$), metal halide, mercury (Hg), cadmium (Cd), zinc (Zn), tin (Sn), gallium (Ga), iron (Fe), lithium (Li), sodium (Na), excimer-forming gas, air, steam, metal oxide, aerosol, a fluid medium, and a regenerating medium.

However, the medium material for plasma ignition is not limited thereto. The medium material for plasma ignition may be generated by using a solid or liquid target (not illustrated) (hereinafter referred to as "target") formed within the chamber 130. For example, the medium material for plasma ignition may be generated by irradiating a laser beam on the target formed within the chamber 130. The target may be a metal pool or a metal film. The target may be a solid or a liquid that is movable within the chamber 130. For example, the target may be a droplet that is movable within the chamber 130.

The medium material for plasma ignition may be a material that is introduced into the chamber 130 and is used to ignite plasma, or may be a material that may easily ignite plasma by using a pulse laser beam, for example, a visible ray pulse laser beam. When the plasma is ignited, high-power energy is supplied to the chamber 130 by the CW laser beam, for example, the IR CW laser beam, thus maintaining the intensity of plasma and maximizing the intensity of plasma.

In the plasma light source 100 according to the present example embodiment, since the plasma ignition is performed by using a pulse laser beam, no electrodes may exist within the chamber 130. Therefore, the plasma light source 100 according to the present example embodiment may be a plasma light source employing an electrodeless lamp or an electrodeless chamber.

The first dichroic mirror 140 may reflect the pulse laser beam input from the pulse laser generator 110 toward the elliptical mirror 160, and may transmit the CW laser beam input from the CW laser generator 120 toward the elliptical mirror 160. The first dichroic mirror 140 is disposed in a direction in which the laser beams of the pulse laser generator 110 and the CW laser generator 120 are emitted. The first dichroic mirror 140 may be disposed such that the pulse laser generator 110 and the CW laser generator 120 maintain a predetermined angle. For example, the pulse laser generator 110 and the CW laser generator 120 may be disposed to maintain substantially 90° with respect to an apex of the first dichroic mirror 140. In addition, the first dichroic mirror 140 may be disposed to have a slope of substantially 45° with respect to traveling directions of the pulse laser beam and the CW laser beam. On the other hand, the arrangement angles of the pulse laser generator 110 and the CW laser generator 120 may be changed. In this case, the slope of the first dichroic mirror 140 may be changed.

The second dichroic mirror 150 may be disposed between the first dichroic mirror 140 and the elliptical mirror 160 and may transmit both the pulse laser beam and the CW laser beam toward the elliptical mirror 160. In addition, the second dichroic mirror 150 may reflect the plasma light discharged from the chamber 130 such that the plasma light is directed toward a homogenizer 240 such as a glass rod lens. More specifically, the plasma light corresponding to the UV rays may be discharged from the chamber 130 and be directly directed toward the homogenizer 240 by the reflection of the second dichroic mirror 150, or may be reflected by the elliptical mirror 160 and then be directed toward the homogenizer 240 by the reflection of the second dichroic mirror 150. The homogenizer 240 may be an optical mechanism that spatially homogenizes light and may not be included as an element of the plasma light source 100 according to the present example embodiment.

On the other hand, the homogenizer 240 may be disposed to substantially be 90° with respect to the elliptical mirror 160, with the second dichroic mirror 150 as an apex. The second dichroic mirror 150 may be disposed to have a slope of substantially 45° with respect to traveling directions of the pulse laser beam, the CW laser beam, and the plasma light, based on reflection and transmission characteristics. The arrangement angle of the homogenizer 240 may be changed. In this case, the slope of the second dichroic mirror 150 may be changed.

The dichroic mirror is a mirror configured by a combination of a plurality of thin films made of materials having different refractive indexes. The dichroic mirror reflects light of a predetermined wavelength and transmits light of the other wavelengths. As compared with a general color filter, the dichroic mirror has very low absorption loss, and a wavelength range of light selectively reflected may be increased or decreased according to a material thickness or a structure of the dichroic mirror.

In the plasma light source 100 according to the present example embodiment, the first dichroic mirror 140 and the second dichroic mirror 150 may be disposed on the same axis with respect to the three kinds of light, for example, the pulse laser beam, the CW laser beam, and the plasma light. In the case of the pulse laser beam, the same axis may be a concept based on the light that is directed toward the elliptical mirror 160 by the reflection of the first dichroic mirror 140, and in the case of the plasma light, the same axis may be a concept based on the light that is directed from the elliptical mirror 160 to the second dichroic mirror 150.

By selectively reflecting or transmitting the light according to a wavelength through the two dichroic mirrors, namely, the first and second dichroic mirrors 140 and 150, which are disposed on the same axis, input light beams incident on the chamber 130 may be combined or synthesized and an output light beam output from the chamber 130 may be separated from the incident input lights. Specifically, the pulse laser beam and the CW laser beam may be input to the chamber 130 through the two dichroic mirrors, namely, the first and second dichroic mirrors 140 and 150, and be synthesized. In addition the plasma light, which is generated in the chamber 130, may be separated from the pulse laser beam and the CW laser beam and be output to the homogenizer 240. Since the plasma light source 100 according to the present example embodiment is configured to input and output light beams through the two dichroic mirrors, namely, the first and second dichroic mirrors 140 and 150, disposed on the same axis, the plasma light source 100 may have a very simple configuration without movement of devices.

The elliptical mirror 160 is configured to surround the chamber 130 and may have a structure that is opened toward the dichroic mirrors 140 and 150. The elliptical mirror 160 may reflect most electromagnetic waves. For example, the elliptical mirror 160 may reflect plasma light corresponding to the pulse laser beam, the CW laser beam, and the UV rays.

The elliptical mirror 160 may have the following law of reflection: That is, light, which is output from one focus of the elliptical mirror 160, is reflected by the elliptical mirror and travels to another focus of the elliptical mirror 160. Accordingly, in a case where the converging point in the chamber 130 is identical to a first focus F1, which is one focus of the elliptical mirror 160, the light incident from a second focus F2, which is another focus of the elliptical mirror 160, is collected at the converging point corresponding to the first focus F1 by the reflection of the elliptical mirror 160, and the light discharged from the converging point travels to the second focus F2 by the reflection of the elliptical mirror 160. For reference, the pulse laser beam input by the reflection of the first dichroic mirror 140 may be regarded as light output from the second focus F2 in terms of the elliptical mirror 160. In practice, the plasma light output by the reflection of the elliptical mirror 160 is also bent by the reflection of the second dichroic mirror 150, but the plasma light may be regarded as traveling toward the second focus F2 in terms of the elliptical mirror 160.

Since the plasma light source 100 according to the present example embodiment employs the elliptical mirror 160, it is possible to maximize the light concentration efficiency of the input light beams, for example, the pulse laser beam and the CW laser beam, in the chamber 130. In addition, it is possible to maximize the output efficiency of the plasma light discharged from the chamber 130 through the elliptical mirror 160.

The first input optical system 170 is an optical system configured to input the pulse laser beam from the pulse laser generator 110 to the first dichroic mirror 140 and may include a pair of axicon lenses 171 and a concave lens 173. The pair of axicon lenses 171 may convert the pulse laser beam into a ring-shaped beam. As illustrated in FIG. 2, the ring-shaped beam means a beam that is distributed in a donut shape or a circular-ring shape on a cross section perpendicular to a traveling direction of light. The ring-shaped beam may be formed using elements other than axicon lenses, for example, a spatial light modulator (SLM).

The concave lens 173 may expand the incident light. For example, when the ring-shaped beam is incident on the concave lens 173, an internal radius (R1 of FIG. 2), an external radius (R2 of FIG. 2), and a width (W1 of FIG. 2) may be expanded. That is, the first input optical system 170 may convert the pulse laser beam into the ring-shaped beam, expand the ring-shaped beam, and input the expanded ring-shaped beam to the first dichroic mirror 140.

For reference, if the pulse laser beam is concentrated, plasma may be generated even in the atmosphere. This is because media for plasma ignition, such as oxygen, nitrogen, and water, exist in the atmosphere. Therefore, by employing the concave lens 173, it is possible to reduce or prevent the generation of plasma in the atmosphere.

In addition, the concave lens 173 may make light appear as if the light is expanded from one point. Accordingly, it may appear as if the pulse laser beam is output from the second focus F2 of the elliptical mirror 160 through the concave lens 173 and the first dichroic mirror 140. As described above, the light output from the second focus F2 travels toward the first focus F1 corresponding to the converging point by the reflection of the elliptical mirror 160. Therefore, the ring-shaped pulse laser beam passing through the concave lens 173 may be concentrated on the converging point of the chamber 130 by the reflection of the elliptical mirror 160.

The second input optical system 180 is an optical system configured to input the CW laser beam from the CW laser generator 120 to the first dichroic mirror 140 and may include a pair of axicon lenses 181, a convex lens 183, and a cylindrical lens 185. As in the first input optical system 170, the pair of axicon lenses 181 may convert the CW laser beam into a ring-shaped beam.

The convex lens 183 may concentrate the incident light. For example, in a case where the ring-shaped beam is input to the convex lens 183, the ring-shaped beam may be contracted to substantially a point. On the other hand, after the incident light is concentrated on the second focus F2 of the elliptical mirror 160, the convex lens 183 makes the incident light be continuously directed toward the elliptical mirror 160. Therefore, the ring-shaped CW laser beam passing through the convex lens 183 may be concentrated on the converging point of the chamber 130 by the reflection of the elliptical mirror 160.

In the case of the CW laser beam input by the second input optical system 180, for example, in the case of the IR CW laser beam, aberration may occur while the CW laser beam is passing through the first dichroic mirror 140 and the second dichroic mirror 150. The cylindrical lens 185 may be disposed so as to correct such aberration. On the other hand, in the case of the pulse laser beam input through the first input optical system 170, aberration may also occur. However, in the case of the pulse laser beam, the cylindrical lens need not be employed because the pulse laser beam is temporarily input for plasma ignition.

The process of generating the plasma light in the plasma light source 100 according to the present example embodiment will be described briefly.

As indicated by a thick arrow of FIG. 1A, the pulse laser beam from the pulse laser generator 110 is converted into the ring-shaped beam through the pair of axicon lenses 171, is expanded through the concave lens 173, and is input to the first dichroic mirror 140. Subsequently, the pulse laser beam is reflected by the first dichroic mirror 140, passes through the second dichroic mirror 150, and is input to the elliptical mirror 160. After that, the pulse laser beam is input to the chamber 130 by the reflection of the elliptical mirror 160, is concentrated on the converging point, and ignites the plasma.

Thereafter, the CW laser beam from the CW laser generator 120 is converted into the ring-shaped beam through the pair of axicon lenses 181, is concentrated through the convex lens 183, and is input to the first dichroic mirror 140 through the cylindrical lens 185. Subsequently, the CW laser beam passes through the first dichroic mirror 140 and the second dichroic mirror 150 and is input to the elliptical mirror 160. After that, the CW laser beam is input to the chamber 130 by the reflection of the elliptical mirror 160, is concentrated on the converging point, maintains the plasma in an ignited state, and increases the intensity of the plasma. After maintaining the plasma and increasing the intensity of the plasma, the input of the pulse laser beam may be stopped.

On the other hand, as indicated by a solid arrow of FIG. 1B, the plasma light (e.g., UV rays) generated by the plasma in the chamber 130 is discharged to the outside of the chamber 130 and is input to the second dichroic mirror 150 by the reflection of the elliptical mirror 160. After that, the plasma light is reflected by the second dichroic mirror 150 and is input to the homogenizer 240. On the other hand, some of the plasma light discharged to the outside may be directly input to the second dichroic mirror 150 without reflection of the elliptical mirror 160 and be input to the homogenizer 240 by the reflection of the second dichroic mirror 150.

In the plasma light source 100 according to the present example embodiment, separate electrodes need not exist in the chamber 130 because the pulse laser beam is used to ignite the plasma and the CW laser beam is used to maintain the plasma in an ignited state and increase the intensity of the plasma. Accordingly, in the plasma light source 100 according to the present example embodiment, it is unnecessary to connect electrodes at the time of replacing the chamber 130 and it is also unnecessary to readjust the position of the chamber 130 because the light-emitting point is not dependent on the position of the chamber 130. Furthermore, since metal parts do not exist in the chamber 130, the lifetime of the chamber 130 may be prolonged.

In addition, by reflecting or transmitting the light according to a wavelength through the two dichroic mirrors, namely, the first and second dichroic mirrors 140 and 150, which are disposed on the same axis, the plasma light source 100 according to the present example embodiment may synthesize input light beams incident on the chamber 130 and separate an output light beam, which is output from the chamber 130, from the incident input lights. Accordingly, the plasma light source 100 according to the present example embodiment may have a simple structure without movement of devices, thus reducing manufacturing costs.

Furthermore, since the plasma light source 100 according to the present example embodiment employs the elliptical mirror 160, it is possible to maximize light concentration efficiency of the input light beams, for example, the pulse laser beam and the CW laser beam, in the chamber 130. In addition, it is possible to maximize the output efficiency of the plasma light discharged from the chamber 130 through the elliptical mirror 160.

The plasma light source 100 according to the present example embodiment may be used in an inspection apparatus or a microscope configured to inspect a wafer, a semiconductor package, a semiconductor chip, or a display panel during a semiconductor manufacturing process. In addition, the plasma light source 100 according to the present example embodiment may be used as a light source in an exposure process.

FIGS. 3 to 8 are schematic diagrams of plasma light sources 100a to 100f according to example embodiments of the inventive concept. For convenience, the description provided above with reference to FIGS. 1A and 1B will not be repeated again.

Figure 3:
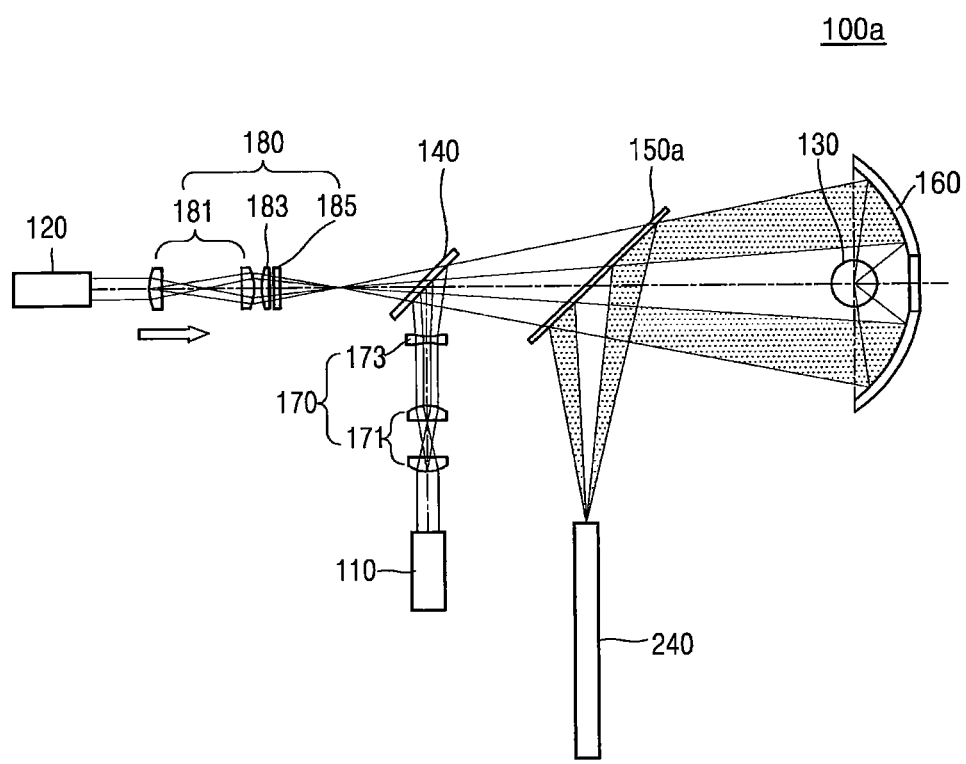
FIGS. 3 to 8 are schematic diagrams of plasma light sources according to example embodiments of the inventive concept.

Referring to FIG. 3, the plasma light source 100a according to the present example embodiment may differ from the plasma light source 100 of FIG. 1A in terms of an arrangement angle of a second dichroic mirror 150a. Specifically, in the plasma light source 100a according to the present example embodiment, the second dichroic mirror 150a may be disposed to reflect plasma light in a downward direction. Accordingly, in order to receive the plasma light reflected from the second dichroic mirror 150a, a homogenizer 240 may be disposed under the second dichroic mirror 150a, as illustrated in FIG. 3.

As illustrated in FIG. 3, an inclination direction of the second dichroic mirror 150a may be identical to an inclination direction of the first dichroic mirror 140. In addition, the inclination angle of the second dichroic mirror 150a may be identical to or different from the inclination angle of the first dichroic mirror 140. As described above, the inclination angles of the first dichroic mirror 140 and the second dichroic mirror 150*a* may be changed according to the arrangement positions of the pulse laser generator 110 and the homogenizer 240.

Figure 4:
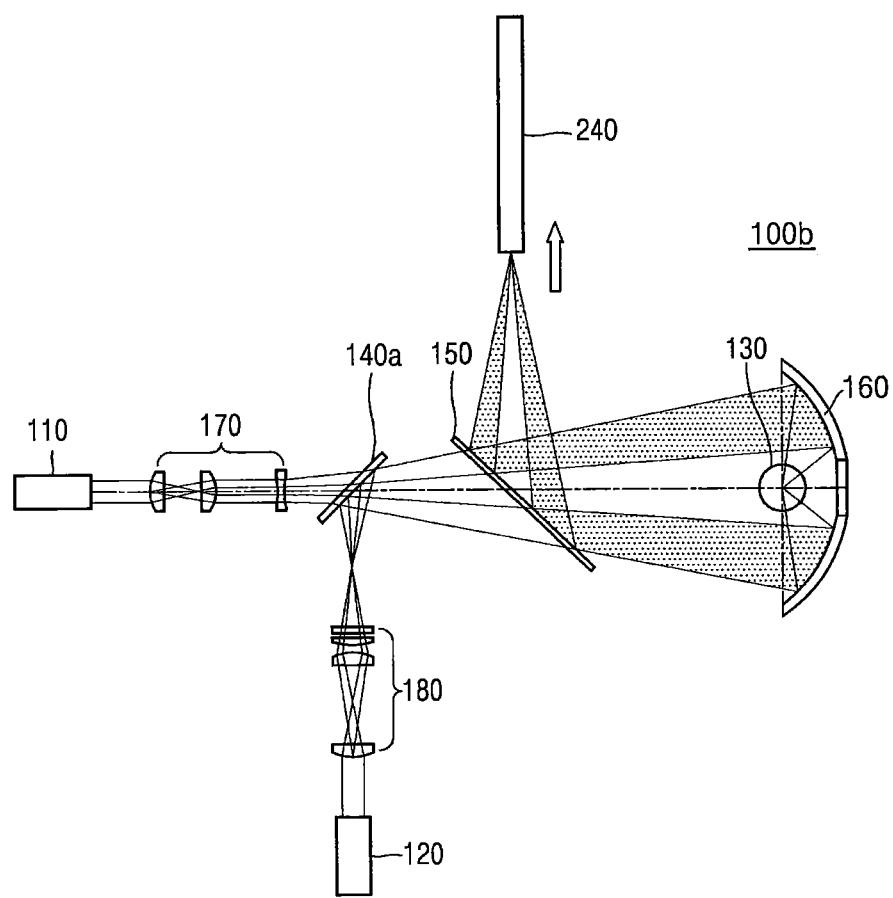

Referring to FIG. 4, the plasma light source 100*b* according to the present example embodiment differs from the plasma light source 100 of FIG. 1A in that a pulse laser generator 110 and a first input optical system 170 change positions thereof with those of a CW laser generator 120 and a second input optical system 180, respectively. Specifically, the pulse laser generator 110 and the first input optical system 170 may be disposed on a left front side of a first dichroic mirror 140*a*, and the CW laser generator 120 and the second input optical system 180 may be disposed under the first dichroic mirror 140*a*.

On the other hand, due to the change in positions, reflection and transmission characteristics of the first dichroic mirror 140*a* may also be changed. For example, the first dichroic mirror 140*a* may transmit the pulse laser beam, for example, the visible ray pulse laser beam, and direct the pulse laser beam toward the second dichroic mirror 150. In addition, the first dichroic mirror 140*a* may reflect the CW laser beam, for example, the IR CW laser beam, and direct the CW laser beam toward the second dichroic mirror 150.

In other words, the arrangement positions of the pulse laser generator 110 and the CW laser generator 120 may be changed according to the reflection and transmission characteristics of the first dichroic mirror 140*a*. Furthermore, as the arrangement positions of the pulse laser generator 110 and the CW laser generator 120 are changed, the arrangement positions of the first input optical system 170 and the second input optical system 180 may also be changed. The configurations and functions of the first input optical system 170 and the second input optical system 180 are the same as those described above with reference to FIGS. 1A and 1B.

Figure 5:
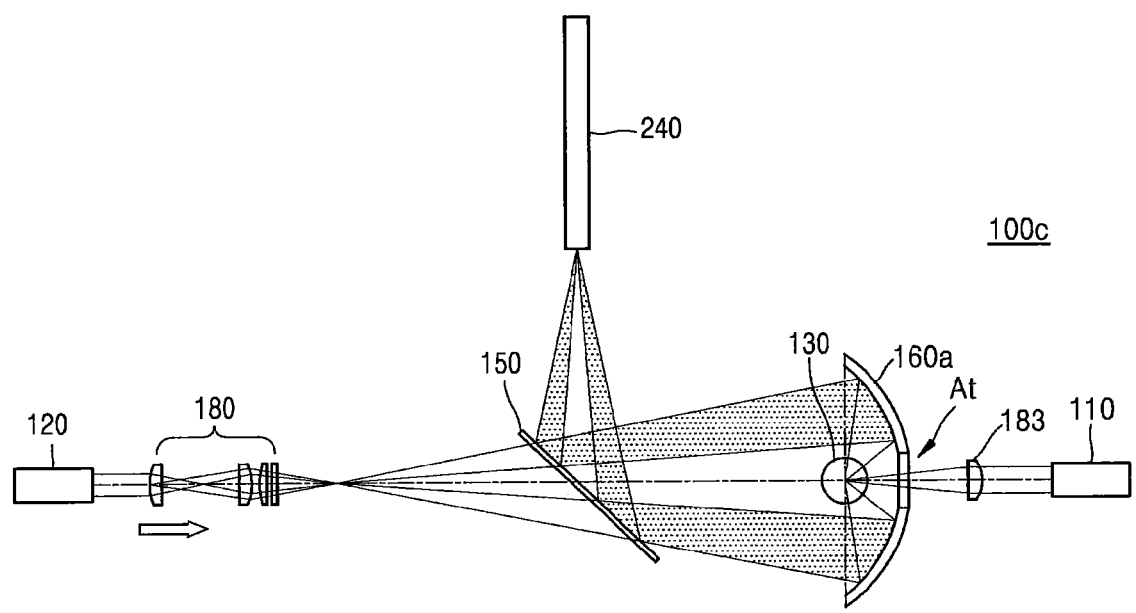

Referring to FIG. 5, the plasma light source 100*c* according to the present example embodiment may differ from the plasma light source 100 of FIG. 1A in terms of an input structure of a pulse laser beam and a configuration of dichroic mirrors.

Specifically, in the plasma light source 100*c* according to the present example embodiment, the pulse laser beam from the pulse laser generator 110 disposed on a right rear side of the elliptical mirror 160*a* may be directly input to the chamber 130 through the convex lens 183. In order to directly input the pulse laser beam to the chamber 130, a transmission area At such as a lens or a window capable of transmitting the pulse laser beam may be formed in the elliptical mirror 160*a*. In some cases, the transmission area At may have a through-hole shape without separate material layers. The pulse laser beam may be concentrated on the converging point of the chamber 130 by the convex lens 183. Therefore, the pulse laser beam may ignite the plasma in the chamber 130 as in the plasma light source 100 of FIG. 1A.

In addition, in the plasma light source 100*c* according to the present example embodiment, only the second dichroic mirror 150*a* may be included and the first dichroic mirror 140 may be omitted. In other words, the main function of the first dichroic mirror 140 is to input the pulse laser beam. In the plasma light source 100*c* according to the present example embodiment, the first dichroic mirror may need not exist because the pulse laser beam is directly input from the rear of the elliptical mirror 160*a*.

The CW laser beam from the CW laser generator 120 is input to the second dichroic mirror 150 through the second input optical system 180, passes through the second dichroic mirror 150, and is reflected by the elliptical mirror 160*a*. Thus, the CW laser beam may be concentrated on the converging point of the chamber 130, maintain the plasma in an ignited state, and increase the intensity of the plasma. On the other hand, as in the plasma light source 100 of FIG. 1A, the plasma light discharged from the chamber 130 may be input to the homogenizer 240 by the reflection of the elliptical mirror 160*a* and the reflection of the second dichroic mirror 150.

Figure 6:
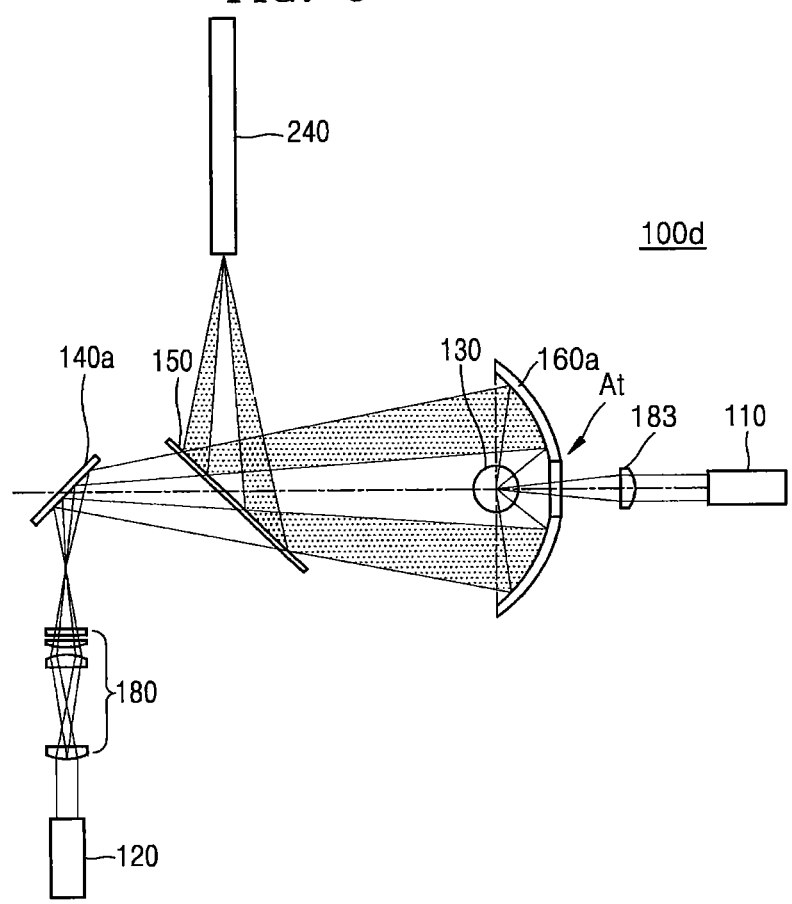

Referring to FIG. 6, the plasma light source 100*d* according to the present example embodiment may differ from the plasma light source 100*c* of FIG. 5 in that a CW laser beam is input to a chamber 130 by the reflection of a first dichroic mirror 140*a*. Specifically, similar to the plasma light source 100*c* of FIG. 5, the plasma light source 100*d* according to the example embodiment may be configured such that a pulse laser beam is directly input to a right rear side of an elliptical mirror 160*a*. However, the plasma light source 100*d* according to the present example embodiment may further include the first dichroic mirror 140*a* disposed on a left front side of a second dichroic mirror 150, and the CW laser beam may be input to the chamber 130 by the reflection of the first dichroic mirror 140*a*.

In other words, the CW laser beam from the CW laser generator 120 is input to the first dichroic mirror 140*a* through the second input optical system 180, is reflected by the first dichroic mirror 140*a*, and is input to the elliptical mirror 160*a*. After that, the CW laser beam may be reflected by the elliptical mirror 160*a*, is input to the chamber 130, and be concentrated on the converging point of the chamber 130.

Figure 7:
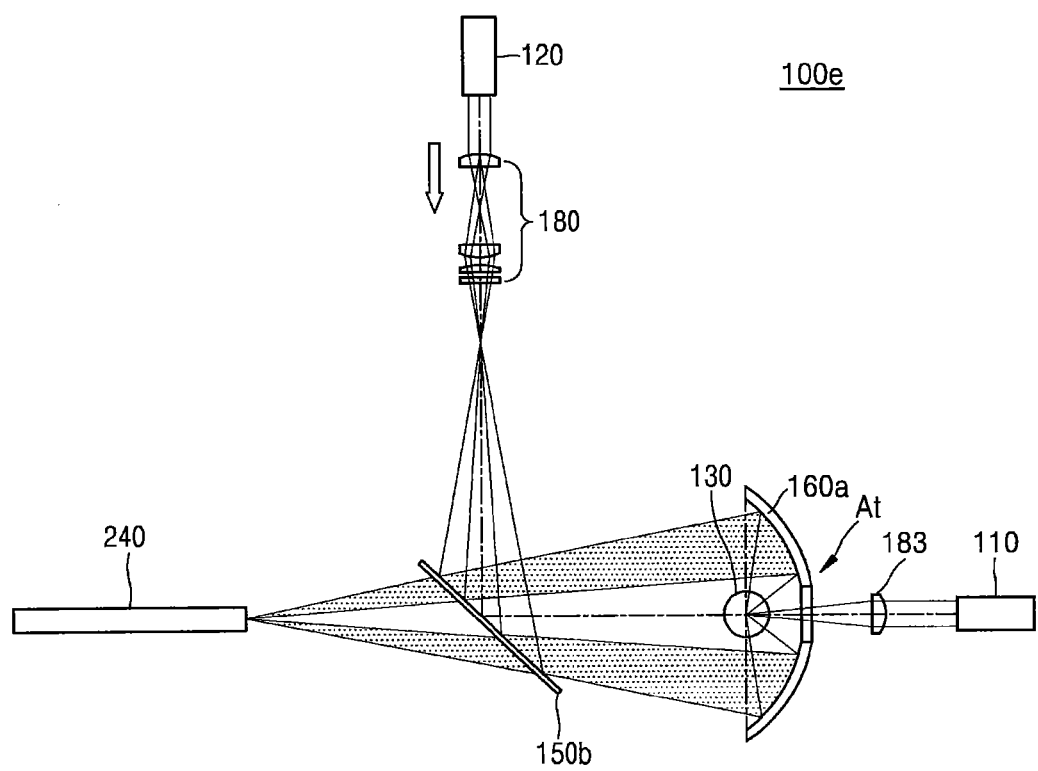

Referring to FIG. 7, the plasma light source 100*e* according to the present example embodiment may differ from the plasma light source 100*c* of FIG. 5 in terms of reflection and transmission characteristics of a second dichroic mirror 150*b*. For example, in the plasma light source 100*e* according to the present example embodiment, the second dichroic mirror 150*b* may have characteristics that transmit the plasma light (e.g., UV rays) and reflect the CW laser beam (e.g., IR CW laser beam). Accordingly, the CW laser generator 120 and the second input optical system 180 may be disposed above the second dichroic mirror 150*b*, and the homogenizer 240 may be disposed on the left front side of the second dichroic mirror 150*b*.

Specifically, the CW laser beam from the CW laser generator 120 may be input to the elliptical mirror 160*a* by the reflection of the second dichroic mirror 150*b* and be concentrated on the converging point of the chamber 130 by the reflection of the elliptical mirror 160*a*. On the other hand, the plasma light (e.g., UV rays) discharged to the outside may be directed toward the second dichroic mirror 150*b* by the reflection of the elliptical mirror 160*a*, pass through the second dichroic mirror 150*b*, and be input to the homogenizer 240.

Figure 8:
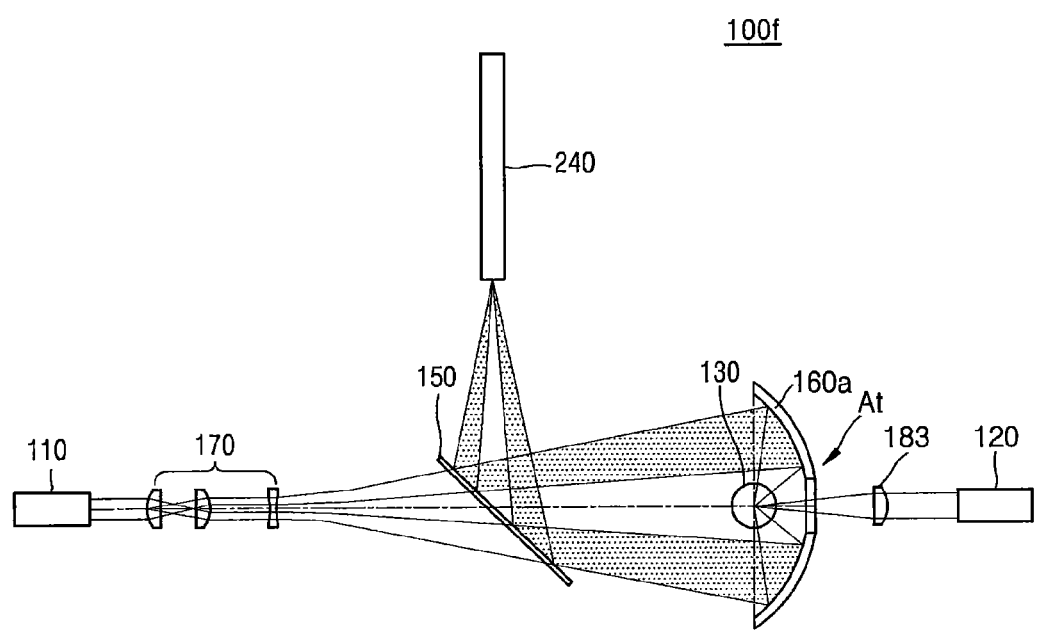

Referring to FIG. 8, the plasma light source 100*f* according to the present example embodiment may differ from the plasma light source 100*c* of FIG. 5 in that the pulse laser generator 110 changes a position thereof with that of a CW laser generator 120.

In the plasma light source 100*f* according to the present example embodiment, the pulse laser generator 110 and a first input optical system 170 may be disposed on a left front side of a second dichroic mirror 150, and the CW laser generator 120 may be disposed on a right rear side of an elliptical mirror 160*a*. Under such an arrangement configuration, the pulse laser beam from the pulse laser generator 110 is input to the second dichroic mirror 150 through the first input optical system 170, passes through a second dichroic mirror 150, and is input to the elliptical mirror 160a. After that, the pulse laser beam is input to a chamber 130 by the reflection of the elliptical mirror 160a and is concentrated on a converging point, and thus, the pulse laser beam is capable of igniting plasma.

On the other hand, the CW laser beam from the CW laser beam generator 120 is concentrated on the converging point of the chamber 130 through a transmission area At of the elliptical mirror 160a by a convex lens 183, thus maintaining the plasma in an ignited state and increasing the intensity of the plasma. In addition, as in the plasma light source 100c of FIG. 5, the plasma light discharged from the chamber 130 may be input to a homogenizer 240 by the reflection of the elliptical mirror 160a and the reflection of the second dichroic mirror 150.

Figure 9:
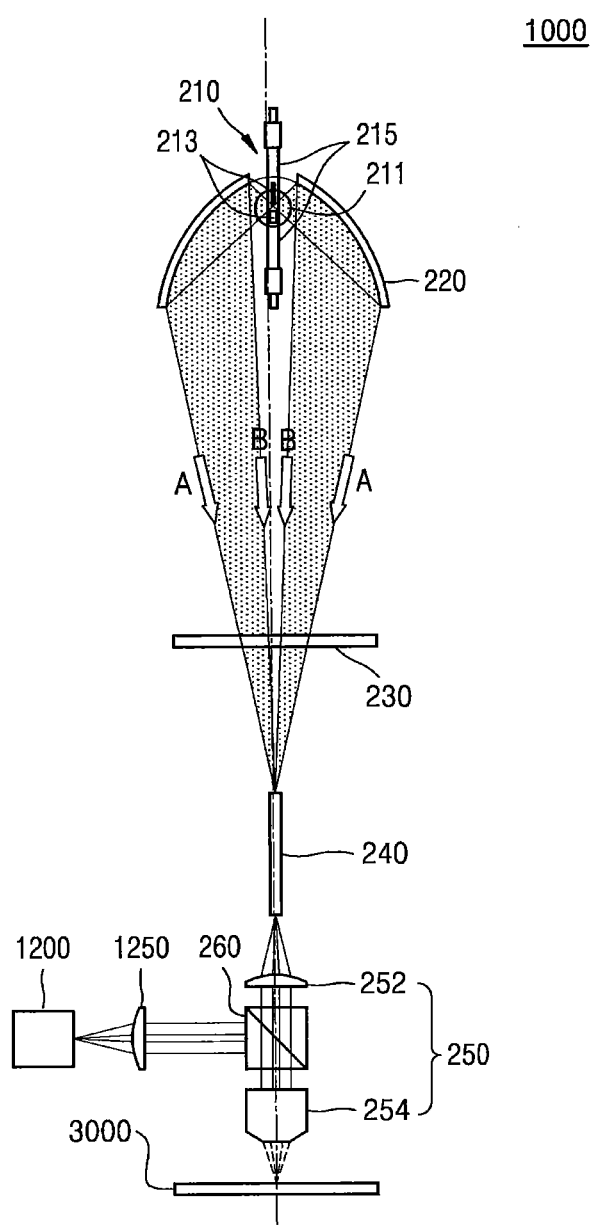
FIG. 9 is a schematic diagram of an inspection apparatus including an illumination optical system according to example embodiments of the inventive concept.

FIG. 9 is a schematic diagram of an inspection apparatus 1000 including an illumination optical system, according to an example embodiment of the inventive concept.

Referring to FIG. 9, the inspection apparatus 1000 according to the present example embodiment may include a light source 210, an elliptical mirror 220, a neutral density (ND) filter 230, a homogenizer 240, a first optical system 250, a beam splitter 260, a second optical system 1250, and a detector 1200. The inspection apparatus 1000 may be an apparatus for inspecting a wafer, a semiconductor package, a semiconductor chip, a display panel, or the like in a semiconductor manufacturing process. In addition, the inspection apparatus 1000 may be a microscope. The light source 210, the elliptical mirror 220, the ND filter 230, the homogenizer 240, the first optical system 250, and the beam splitter 260 may correspond to an illumination optical system that irradiates light on an inspection object 3000, and the second optical system 1250 and the detector 1200 may correspond to a detection optical system that detects light reflected from the inspection object 3000.

The light source 210 may be a plasma light source. For example, as illustrated in FIG. 9, the light source 210 may be a plasma light source including a short arc discharge lamp. However, the light source 210 according to the present example embodiment is not limited to a short arc discharge lamp. Examples of the light source 210 may include any types of plasma light sources that ignite plasma by using various ignition sources, such as microwaves, UV rays, high-frequency waves, a flash lamp, a pulse laser beam, or a pulse lamp. Furthermore, the light source 210 is not limited to a plasma light source and may include a laser beam light source or a light-emitting diode (LED) light source.

The light source 210 having the short arc lamp structure may include a chamber 211 in which a medium for plasma generation is sealed and plasma is ignited, a pair of electrodes 213 protruding inward from the chamber 211 so as to cause discharge in the chamber 211, and a pair of legs 215 that supports the chamber 211 and provide an extension passage of the electrodes 213.

The elliptical mirror 220 may be treated as an element of the light source 210 or may be treated as an element separate from the light source 210. The elliptical mirror 220 may reflect light generated by the light source 210 and concentrate the reflected light on the homogenizer 240.

On the other hand, when the light is concentrated by the elliptical mirror 220, the spatial light intensity on an incidence surface of the homogenizer 240 may appear as a Gaussian distribution. If light having different spatial intensities is directly used as an illumination of a microscope or an inspection apparatus, a bright region and a dark region occur. A difference of brightness in these regions may cause a great problem in the microscope or the inspection apparatus. A spatial intensity distribution of light may be homogenized in a relatively simple manner by passing the light through the homogenizer 240. However, when passes through the homogenizer 240, the light repeats only a total reflection therein. Hence, an incidence angle of the light to the homogenizer 240 is equal to an exit angle of the light from the homogenizer 240. Therefore, the homogenizer 240 may not homogenize a light intensity distribution in terms of angle. The angle may mean an angle (e.g., a solid angle) that increases as a distance from a center of a concentric circle increases on a cross section perpendicular to a traveling direction of the light.

Due to the configuration of the elliptical mirror 220, the intensity of reflected light around the hole of the center (arrow B) is highest and the intensity of light is gradually weaker toward an outer periphery (arrow A). Thus, it can be seen that the intensity of light is greatly dependent on the incidence angle of the light. Therefore, even when the light reflected from the elliptical mirror 220 passes through the homogenizer 240, the light intensity distribution in terms of angle may be non-uniform.

The ND filter 230 may reduce the light transmittance as a distance to the center decreases. For example, when the light passes through the ND filter 230, the light transmittance is low in the center and the light transmittance is high in the outer periphery. Therefore, if the light having high intensity in the center and low intensity in the outer periphery passes through the ND filter 230, overall uniform light may be generated due to transmittance characteristics of the ND filter 230.

The ND filter 230 is also called an ND gradient filter or a gradient ND filter. The function of the ND filter 230 is described below in more detail with reference to FIGS. 10 to 12.

The homogenizer 240 may spatially homogenize the intensity of light through total reflection. However, due to the total reflection characteristic, the intensity of light may not be homogenized in terms of angle.

The first optical system 250 may include a collimation lens 252 and an objective lens 254. The collimation lens 252 may convert light output from the homogenizer 240 into parallel light. The collimation lens 252 may have a tube lens shape. The objective lens 254 concentrates the parallel light from the collimation lens 252 and irradiates the concentrated parallel light on the inspection object 3000.

The inspection object 3000 may be various devices to be inspected, such as a wafer, a semiconductor package, a semiconductor chip, and a display panel. The inspection object 3000 may be disposed and supported on an inspection stage (not illustrated) that is movable in x, y, and z directions.

The beam splitter 260 may transmit the parallel light from the collimation lens 252 and transfer the parallel light to the objective lens 254. In addition, the beam splitter 260 may reflect the light, which is reflected from the inspection object 3000 and transferred through the objective lens 254, and transfers the reflected light to the second optical system 1250. The beam splitter 260 may be a type of dichroic mirror. On the other hand, the beam splitter 260 may reflect the parallel light from the collimation lens 252 and transmit the reflected light from the objective lens 254 according to reflection and transmission characteristics of the beam splitter 260. In this case, the light source 210, the elliptical mirror 220, the ND filter 230, and the collimation lens 252 may be disposed on the side of the beam splitter 260, and the second optical system 1250 and the detector 1200 may be disposed above the beam splitter 260 so as to be on the same line as the inspection object 3000.

The second optical system 1250 may transfer the reflected light received from the beam splitter 260 to the detector 1200. The second optical system 1250 may be a relay lens.

The detector 1200 may receive the reflected light from the second optical system 1250 and transfer the reflected light to other analysis devices (not illustrated) for analyzing the reflected light. In some cases, the detector 1200 may include an analyzer or may interwork with an analyzer to analyze the reflected light. The detector 1200 may be a charge-coupled device (CCD) camera. The detector 1200 is not limited to a CCD camera and may adopt various sensors, including a complementary metal-oxide semiconductor (CMOS) image sensor.

By employing the ND filter 230, the illumination optical system or the inspection apparatus according to the present example embodiment may homogenize the intensity distribution of the light reflected from the elliptical mirror 220 in terms of angle. Specifically, as described above, in the case of using the elliptical mirror 220, the intensity of light is weak in the periphery, depending on the incidence angle. Thus, the light intensity distribution may be non-uniform in terms of angle. That is, the intensity of light may be high in the central area and low in the outer peripheral area on the cross section perpendicular to the traveling direction of the light. When the light having the above-described distribution passes through the ND filter 230, the intensity of light is low in the central area due to the characteristics of the ND filter 230. Thus, the light passing through the ND filter 230 may have a uniform light intensity distribution in terms of angle.

For reference, a method of using an optical fiber may be taken into account so as to improve the uniformity of the light intensity distribution in terms of angle. However, the optical fiber is usable only when the output of a visible ray range is low, and is difficult to use in the case of high-power UV rays. Since the UV rays have a low transmittance with respect to the optical fiber, optical loss is high. In addition, when the UV rays are incident, the optical fiber may be damaged. Hence, the optical fiber may not be used for high-brightness UV rays such as the plasma light.

Figure 10:
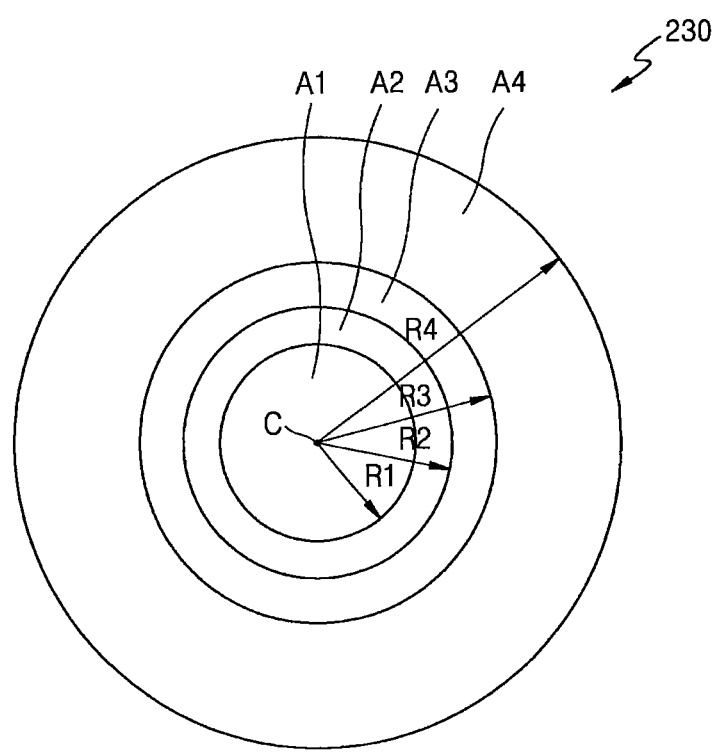
FIG. 10 is a schematic diagram illustrating transmittance according to a position of a neutral density filter employed in the inspection apparatus of FIG. 9.

FIG. 10 is a conceptual diagram for describing transmittance according to the position of the ND filter 230 employed in the inspection apparatus 1000 of FIG. 9.

Referring to FIG. 10, the ND filter 230 may have transmittance symmetrically varying about a center point C. For example, the ND filter 230 may be divided into a first area A1 from the center point C to a first radius R1, a second area A2 from an outer boundary of the first area A1 to a second radius R2, a third area A3 from an outer boundary of the second area A2 to a third radius R3, and a fourth area A4 from an outer boundary of the third area A3 to a fourth radius R4. The first radius R1, the second radius R2, the third radius R3, and the fourth radius R4 may be about 36 mm, about 48 mm, about 60 mm, and about 100 mm, respectively. In addition, the transmittance of the first area A1, the transmittance of the second area A2, the transmittance of the third area A3, and the transmittance of the fourth area A4 may be about 35%, about 45%, about 60%, and about 98%, respectively. The area division of the ND filter 230 and the transmittance of each area are not limited to the above examples and may be variously changed.

When light having a uniform intensity distribution as a whole passes through the ND filter 230, the transmitted light may have a light intensity distribution that gradually increases toward the outer periphery, that is, the fourth area A4. On the other hand, in the case of the light having a light intensity distribution that is high in the central area and low in the outer peripheral area, if the light passes through the ND filter 230, it is possible to obtain a uniform light intensity distribution as a whole. Therefore, angularly uniform light may be obtained by applying the ND filter 230 to angularly non-uniform light that is reflected by the elliptical mirror 220.

Figure 11A:
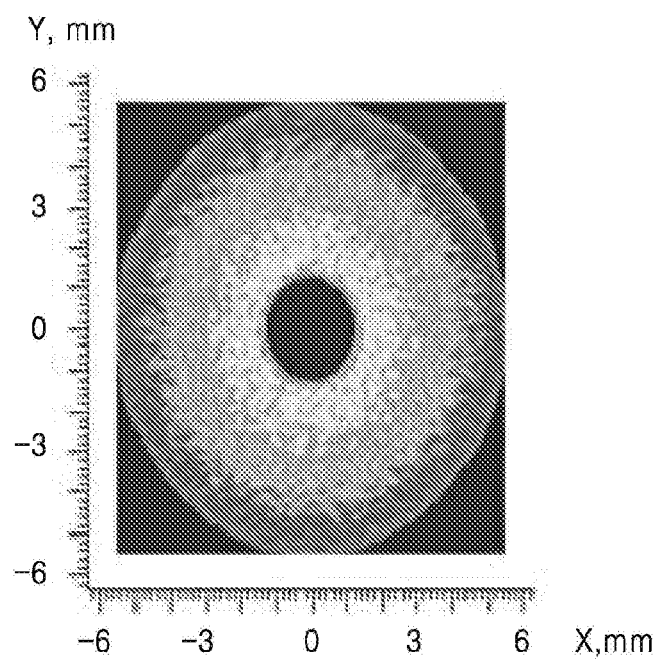
FIG. 11A is a simulation image of a light intensity distribution when the neutral density filter is omitted from the inspection apparatus of FIG. 9.
Figure 11B:
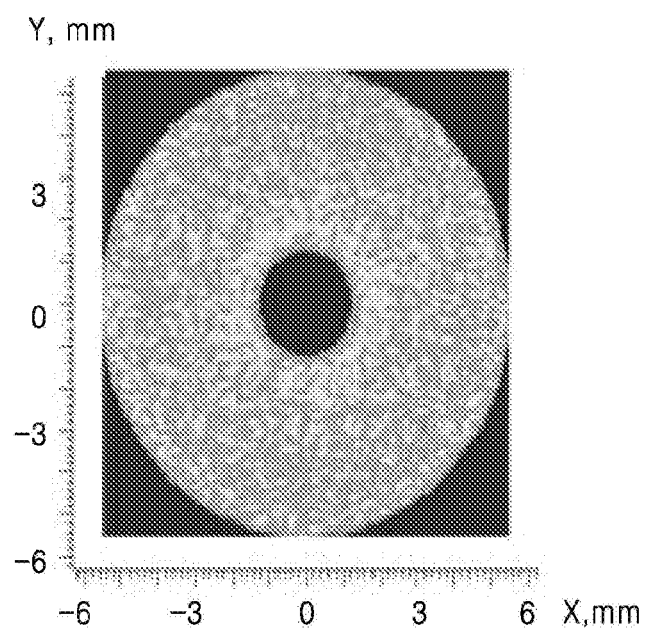
FIG. 11B is a simulation image of a light intensity distribution when the neutral density filter is present in the inspection apparatus of FIG. 9.

FIG. 11A is a simulation photograph of a light intensity distribution when the ND filter 230 is omitted from the inspection apparatus 1000 of FIG. 9, and FIG. 11B is a simulation photograph of a light intensity distribution when the ND filter 230 is present in the inspection apparatus 1000 of FIG. 9. FIGS. 11A and 11B illustrate light intensity distributions on a pupil surface under the collimation lens 252 of the inspection apparatus 1000 of FIG. 9.

Referring to FIG. 11A, when the ND filter 230 is omitted, the intensity of light is gradually weaker as a distance increases from the central area to the outer peripheral area. However, as illustrated in FIG. 11B, when the ND filter 230 is present, the intensity of light is uniform as a whole. A bright area has high intensity of light and a dark area has low intensity of light.

For reference, in the images of FIGS. 11A and 11B, no light is present in dark areas existing in the central area and the outer peripheral area, which may be caused by the configurations of the light source 210 and the elliptical mirror 220. For example, as illustrated in FIG. 9, when the light source 210 has a short arc discharge lamp structure, the portions corresponding to the legs 215 block the light, and thus, no light exists in the central area. In addition, only the light reflected by the elliptical mirror 220 is concentrated on the homogenizer 240, and the remaining light is blocked. Thus, no light exists in the outer peripheral area corresponding to the outside of the elliptical mirror 220.

FIGS. 12A and 12B are graphs of light intensity distributions in an X slice and a Y slice. The graphs of FIGS. 12A and 12B correspond to the images of FIGS. 11A and 11B, respectively.

Referring to FIG. 12A, when the ND filter 230 is omitted, the intensity of light is gradually weaker as a distance increases from the central area to the outer peripheral area. However, as illustrated in FIG. 12B, when the ND filter 230 is present, there is no great difference in the intensity of light between the central area and the outer peripheral area.

When numerically comparing the intensity of light in the graph of FIG. 12B with the intensity of light in the graph of FIG. 12A, the overall intensity of light in the graph of FIG. 12B is similar to the intensity of light in the outer peripheral area of the graph of FIG. 12A. As a result, the inspection apparatus 1000 according to the present example embodiment reduces the intensity of light in the central area by employing the ND filter 230, thus homogenizing the overall intensity of light. The central area Ac having low intensity of light corresponds to the central area where no light exists in the images of FIGS. 11A and 11B.

Figure 13:
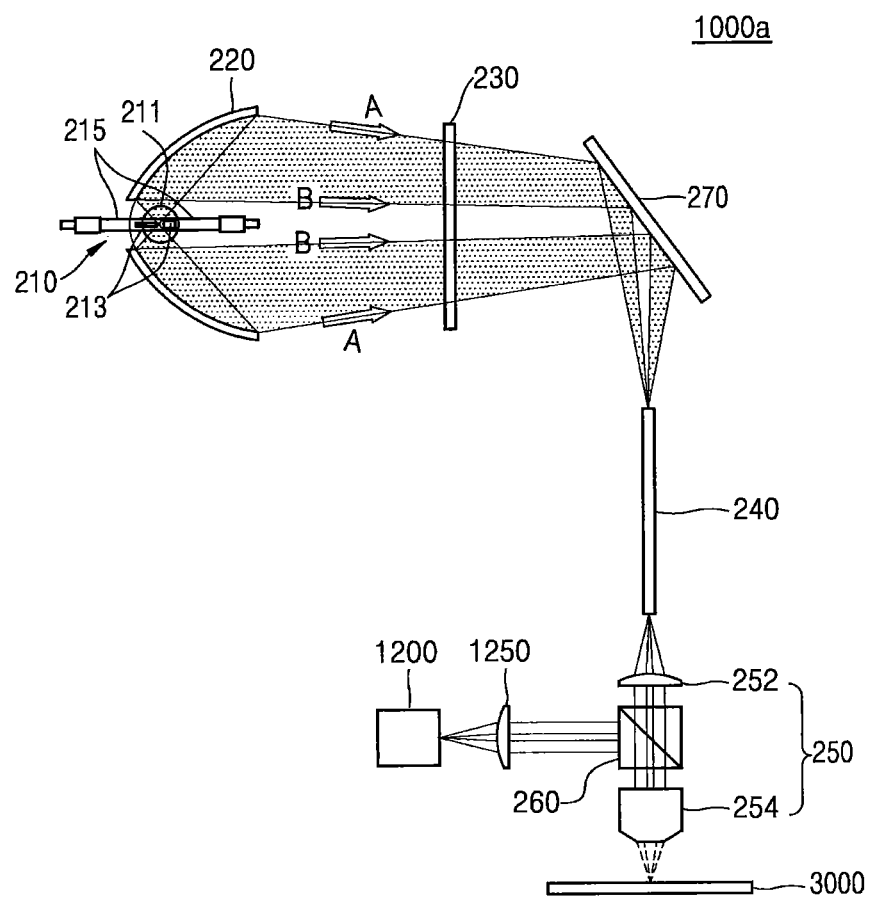
FIGS. 13 to 15 are schematic diagrams of inspection apparatuses including an illumination optical system, according to example embodiments of the inventive concept.
Figure 14:
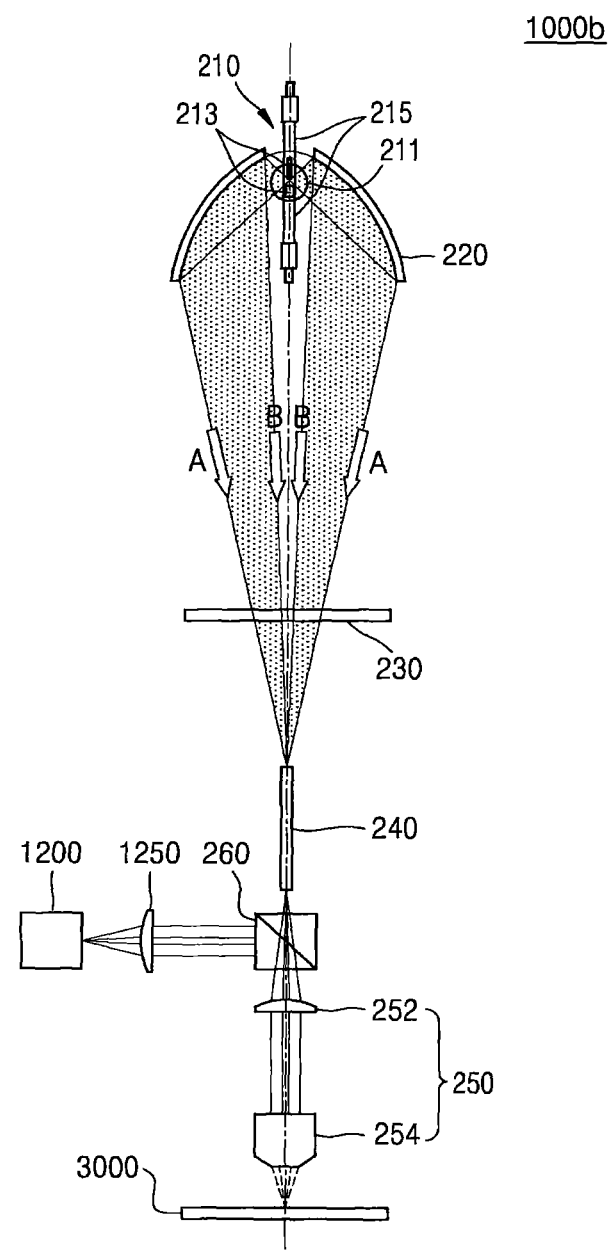
Figure 15:
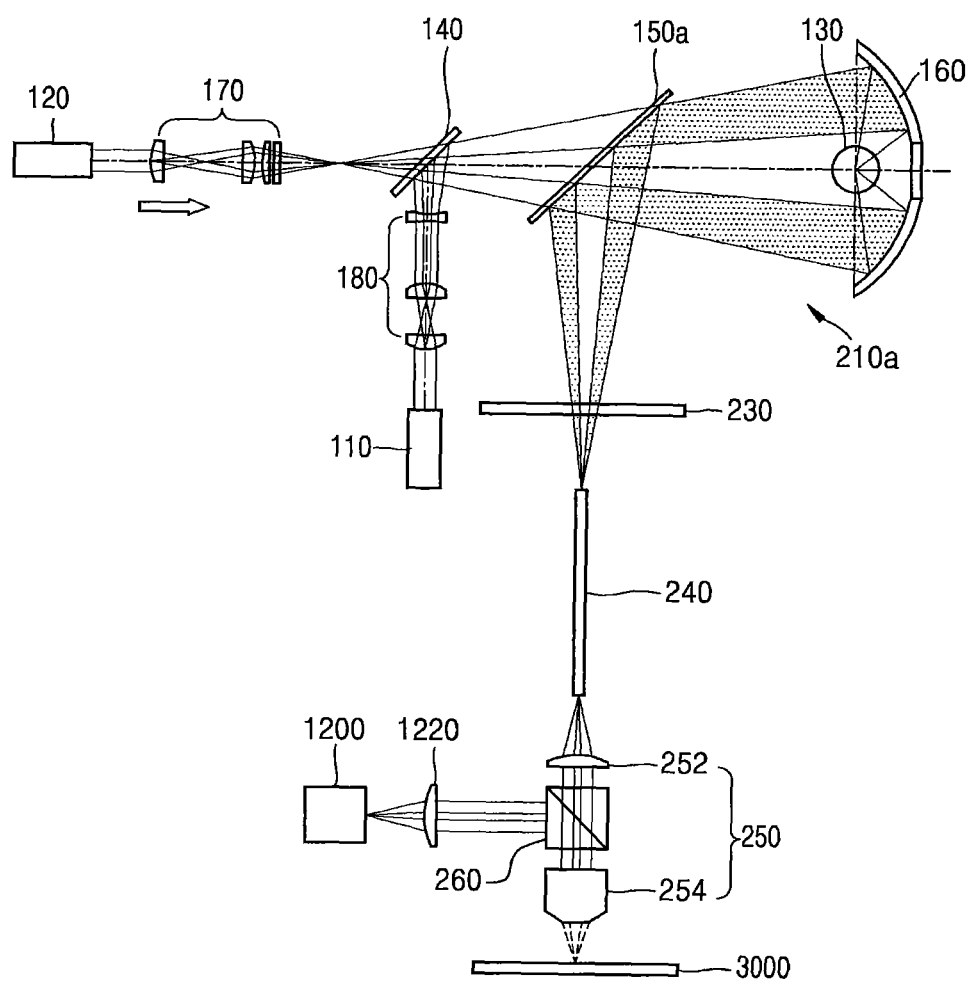

FIGS. 13 to 15 are schematic diagrams of inspection apparatuses 1000*a*, 1000*b*, and 1000*c* including an illumination optical system, according to example embodiments of the inventive concept. For convenience, the description provided above with reference to FIG. 9 will not be repeated again.

Referring to FIG. 13, the inspection apparatus 1000*a* according to the present example embodiment differs from the inspection apparatus 1000 of FIG. 9 in that a mirror 270 is further included and arrangements of elements are changed accordingly. Specifically, the mirror 270 may be disposed on a right rear side of an ND filter 230, and a light source 210, an elliptical source 220, and the ND filter 230 may be disposed on a left front side of the mirror 270. The mirror 270 disposed as above may reflect light incident from the left side and direct the light in a downward direction. On the other hand, a homogenizer 240, a first optical system 250, and a beam splitter 260 may be disposed under the mirror 270, and a second optical system 1250 and a detector 1200 may be disposed on a side of the beam splitter 260.

By employing the mirror 270, the inspection apparatus 1000a according to the present example embodiment may increase the degree of freedom of space arrangement of elements, thus making the inspection apparatus 1000a more compact.

Referring to FIG. 14, the inspection apparatus 1000b according to the present example embodiment differs from the inspection apparatus 1000 of FIG. 9 in terms of an arrangement position of a beam splitter 260. The beam splitter 260 in the inspection apparatus 1000 of FIG. 9 is disposed between the collimation lens 252 and the objective lens 254, but the beam splitter 260 in the inspection apparatus 1000b of FIG. 14 may be disposed between a homogenizer 240 and a collimation lens 252.

The beam splitter 260 simply separates light irradiated on an inspection object 3000 and light reflected from the inspection object 3000. Thus, the inspection apparatus 1000b may not be greatly influenced wherever the beam splitter 260 is disposed above or under the collimation lens 252. The position of the second optical system 1250 and the detection 1200, which receive the reflected light from the beam splitter 260, may be also changed according to the arrangement position of the beam splitter 260.

Referring to FIG. 15, the inspection apparatus 1000c according to the present example embodiment differs from the inspection apparatus 1000 of FIG. 9 in terms of a type of a light source 210a. For example, the light source 210a may have the same configuration as the plasma light source 100 described with reference to FIGS. 1A and 1B, instead of a short arc discharge lamp. More specifically, the light source 210a may include a pulse laser generator 110, a CW laser generator 120, a chamber 130, a first dichroic mirror 140, a second dichroic mirror 150a, an elliptical mirror 160, a first input optical system 170, and a second input optical system 180.

A pulse laser beam (e.g., visible ray pulse laser beam) from the pulse laser generator 110 may be input to the chamber 130 and ignite plasma. A CW laser beam (e.g., IR CW laser beam) from the CW laser generator 120 may be input to the chamber 130, maintain the plasma in an ignited state, and increase the intensity of plasma. Plasma light (e.g., UV rays) discharged from the chamber 130 may be reflected toward the second dichroic mirror 150a by the elliptical mirror 160 and be reflected toward the ND filter 230 by the second dichroic mirror 150a. Subsequent traveling processes of the output light may be substantially the same as those described above with reference to FIG. 9.

Since the inspection apparatus 1000c according to the present example embodiment includes the plasma light source 210a having an electrodeless chamber structure and employs the ND filter 230, it is possible to simplify the light source structure and homogenize the light intensity distribution in terms of angle.

In the inspection apparatus 1000c according to the present example embodiment, the plasma light source 100 of FIGS. 1A and 1B is used as the light source 210a, but any one of the plasma light sources 100a to 100f of FIGS. 3 to 8 may be used instead of the light source 100 of FIG. 1A. In addition, in the inspection apparatus 1000c according to the present example embodiment, the light source 210a is not limited to the plasma light sources 100 and 100a to 100f of FIGS. 1A to 8. For example, in the inspection apparatus 1000c according to the example embodiment, examples of the light source 210a may include a plasma light source using various ignition sources, such as microwaves, UV rays, high-frequency waves, a flash lamp, or a pulse lamp. In addition, the light source 210a is not limited to a plasma light source and may be an LED light source or a laser beam light source.

In the inspection apparatus 1000c according to the present example embodiment, the beam splitter 260 may be disposed between the homogenizer 240 and the collimation lens 252, as in the inspection apparatus 1000b of FIG. 14. In addition, as in the inspection apparatus 1000a of FIG. 13, the inspection apparatus 1000c according to the present example embodiment may improve spatial arrangement utilization of elements by employing the mirror 270.

Figure 16:
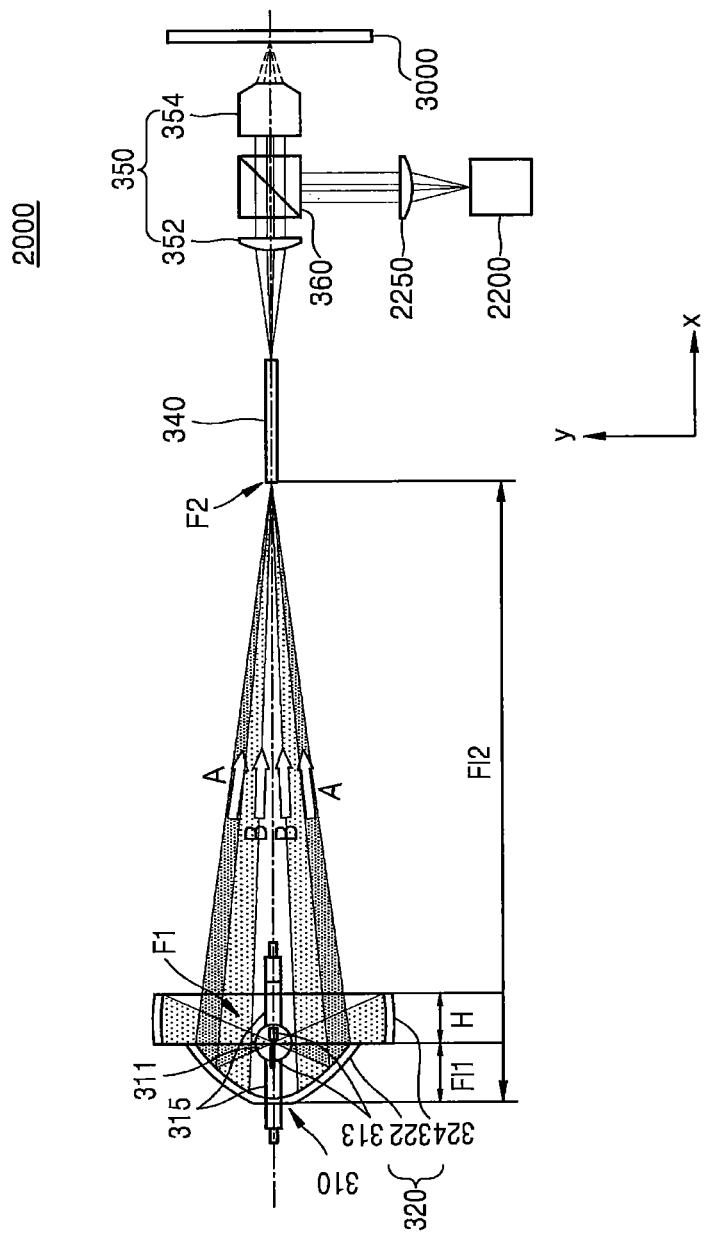
FIG. 16 is a schematic diagram of an inspection apparatus including an illumination optical system, according to another example embodiment of the inventive concept.

FIG. 16 is a schematic diagram of an inspection apparatus 2000 including an illumination optical system, according to another example embodiment of the inventive concept.

Referring to FIG. 16, the inspection apparatus 2000 according to the present example embodiment may include a light source 310, a reflection structure 320, a homogenizer 340, a first optical system 350, a beam splitter 360, a second optical system 2250, and a detector 2200. The light source 310, the reflection structure 320, the homogenizer 340, the first optical system 350, and the beam splitter 360 may correspond to an illumination optical system that irradiates light on an inspection object 3000, and the second optical system 2250 and the detector 2200 may correspond to a detection optical system that detects light reflected from the inspection object 3000.

The light source 310 may be a plasma light source. For example, as illustrated in FIG. 16, the light source 310 may be a plasma light source including a short arc discharge lamp. Similar to the inspection apparatus 1000 of FIG. 9, the light source 310 having the short arc discharge lamp structure may include a chamber 311, a pair of electrodes 313, and a pair of legs 315. However, the light source 310 according to the present example embodiment is not limited to a short arc discharge lamp. Examples of the light source 310 may include any types of plasma light sources that ignite plasma by using various ignition sources, such as microwaves, UV rays, high-frequency waves, a flash lamp, a pulse laser beam, or a pulse lamp. Furthermore, the light source 310 is not limited to a plasma light source and may include a laser light source or an LED light source.

The reflection structure 320 may include an elliptical mirror 322 and a spherical mirror 324. The reflection structure 320 may be treated as an element of the light source 310 or may be treated as an element separate from the light source 310. The reflection structure 320 may reflect light generated by the light source 310 and may homogenize a light intensity distribution in terms of angle and concentrate the reflected light on the homogenizer 340.

The elliptical mirror 322 may reflect light generated by the light source 310 and concentrate the reflected light on the homogenizer 340. However, when the light is concentrated by the elliptical mirror 322 alone, the spatial intensity of light appears as a Gaussian distribution on the incidence surface of the homogenizer 340 and the spatial intensity of light may be homogenized by passing the light through the homogenizer 340. However, as described above, the intensity of light may not be homogenized in terms of angle by the homogenizer 340 due to the total reflection characteristic of the homogenizer 340.

On the other hand, due to the configuration of the elliptical mirror 322, the intensity of reflected light around the hole of the center (arrow B) is highest and the intensity of light is gradually weaker toward the outer periphery (arrow A). Thus, as described above, the intensity of light is greatly dependent on the incidence angle of the light. By applying the elliptical mirror 322 to a microscope, an area where the numerical aperture (NA) is small may be brightly illuminated and an area where the NA is large may be darkly illuminated. In order to increase the resolution of the microscope, light needs to be irradiated uniformly at various angles. In a case of applying to an inspection apparatus, uniformity and higher brightness may be required.

For reference, the characteristics of the elliptical mirror 322 may be determined by the focus of the elliptical mirror 322. For example, as illustrated in FIG. 16, assuming that the center of the chamber 311 is a first focus F1 of the elliptical mirror 322, a distance from the elliptical mirror 322 is a first focal length Fl1, an incidence surface of the homogenizer 340 is a second focus F2, and a distance from the elliptical mirror 322 is a second focal length Fl2, the amount of light concentrated by the elliptical mirror 322 may increase as a ratio of Fl2:Fl1 increases. That is, when the ratio of Fl2:Fl1 increases, the first focus F1 is disposed at a much inner position of the elliptical mirror 322, so that more light is reflected through the elliptical mirror 322.

Due to the elliptical mirror 322, the size of a spot concentrated on a converging point, that is, the second focus F2, increases by Fl2/Fl1 times. Therefore, as the ratio of Fl2:Fl1 increases, the size of the spot increases, causing a reduction in a coupling efficiency between the light and the homogenizer 240. In addition, due to the configuration of the elliptical mirror 322, the intensity of light reflected from the periphery is weak. Thus, the intensity of light is non-uniform according to angles, that is, the intensity of light is non-uniform in terms of angle. The angle may mean an angle (e.g., a solid angle) that increases as a distance from a center of a concentric circle increases on a cross section perpendicular to a traveling direction of the light.

On the contrary, as the ratio of Fl2:Fl1 decreases, a value of Fl2/Fl1 decreases and a small spot may be generated. Therefore, it is possible to increase a coupling efficiency between the light and the homogenizer 240 and to improve light intensity distribution uniformity according to angles. However, if the ratio of Fl2:Fl1 decreases, the amount of light concentrated by the elliptical mirror 322 is reduced as described above. Thus, light utilization efficiency may be reduced.

In order to solve the above-described problem of the elliptical mirror 322, the inspection apparatus 2000 according to the present example embodiment employs the reflection structure 320 in which the spherical mirror 324 is combined with the elliptical mirror 322. More specifically, in the reflection structure 320, the elliptical mirror 322 has a structure that is opened in a direction of the homogenizer 340, that is, a first direction (y direction), the spherical mirror 324 may have a structure that is opened in both directions while surrounding the opening of the elliptical mirror 322. Accordingly, in the spherical mirror 324, the first direction (y direction) may be directed toward the elliptical mirror 322 and a second direction (−y direction) may be directed toward the homogenizer 340.

A first diameter (D1 of FIG. 18) of the opening of the spherical mirror 324 in the first direction may be greater than a second diameter (D2 of FIG. 18) of the opening of the spherical mirror 324 in the second direction. In addition, the first diameter (D1 of FIG. 18) of the opening of the spherical mirror 324 may be greater than a third diameter (D3 of FIG. 18) of the opening of the elliptical mirror 321. The second diameter (D2 of FIG. 18) of the opening of the spherical mirror 324 may be large enough to transmit the light reflected by the elliptical mirror 322 without being blocked. For example, the second diameter D2 of the spherical mirror 324 may be greater than the third diameter D3 of the elliptical mirror 322.

A focal position of the elliptical mirror 322 may match a focal position of the spherical mirror 324. In addition, the chamber 311 may be disposed at the same focus of the elliptical mirror 322 and the spherical mirror 324. However, according to circumstances, the focal position of the elliptical mirror 322 may be different from the focal position of the spherical mirror 324, and the chamber 311 may not be disposed at the same focus of the elliptical mirror 322 and the spherical mirror 324.

In the reflection structure 320 having the above-described configuration, light deviating from the elliptical mirror 322 is reflected toward the elliptical mirror 322 by the spherical mirror 324, and the elliptical mirror 322 reflects the light again and concentrates the light on the homogenizer 340. Thus, it is possible to increase the amount of reflection light and increase light utilization efficiency. In addition, since the light returned by the spherical mirror 324 is reflected at the outer periphery of the elliptical mirror 322, it is possible to increase the intensity of light at the outer periphery of the elliptical mirror 322. Therefore, the reflection structure 320 may contribute to homogenization of the intensity of light in terms of angle. The configuration and function of the reflection structure 320 will be described in more detail with reference to FIGS. 17 to 19.

The homogenizer 340, the first optical system 350, the beam splitter 360, the second beam splitter 1250, and the detector 1200 are substantially identical to those of the inspection apparatus 1000 described above with reference to FIG. 9. As in the inspection apparatus 1000b of FIG. 14, the beam splitter 360 may be disposed between the homogenizer 340 and the collimation lens 352. In addition, as in the inspection apparatus 1000a of FIG. 13, the inspection apparatus 2000 according to the present example embodiment may improve spatial arrangement utilization of elements by employing the mirror 270.

Since the inspection apparatus 2000 according to the present example embodiment includes the reflection structure 320 having a combined structure of the elliptical mirror 322 and the spherical mirror 324, more plasma light discharged from the chamber 311 is reflected and concentrated. Therefore, light utilization efficiency may be increased and the intensity of light at the periphery may be increased, thus homogenizing the light intensity distribution in terms of angle.

In the inspection apparatus 2000 according to the present example embodiment, due to the presence of the spherical mirror 324, the reflection structure 320 may reflect a sufficient amount of light while using the elliptical mirror 322 having a small ratio of Fl2:Fl1. In addition, due to the use of the elliptical mirror 322 having a small ratio of Fl2:Fl1, the spot size of the converging point may be reduced and the brightness may be increased accordingly. As a result, the illumination optical system or the inspection apparatus 2000 according to the present example embodiment may construct an optical system that provides an angularly uniform light intensity distribution with higher brightness, as compared with an illumination optical system or an inspection apparatus using only an elliptical mirror.

Figure 17:
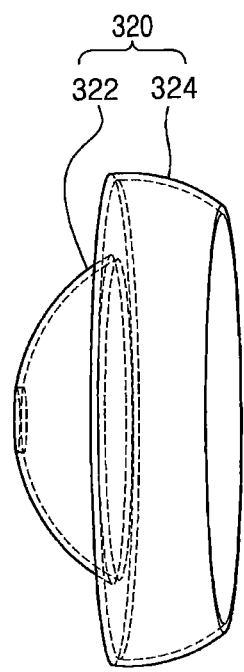
FIGS. 17 to 19 are diagrams illustrating the configuration and function of a reflection structure employed in the inspection apparatus of FIG. 16.
Figure 18:
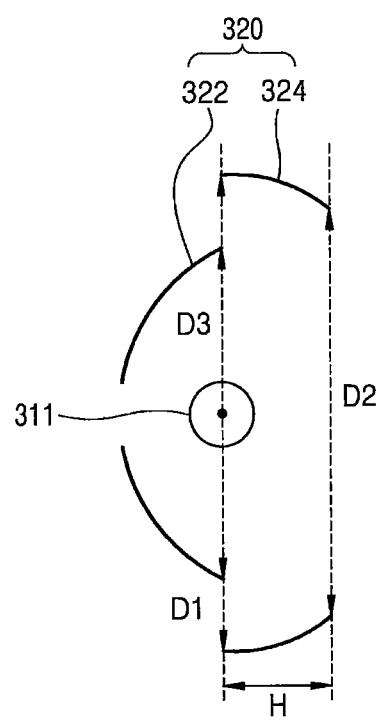
Figure 19:
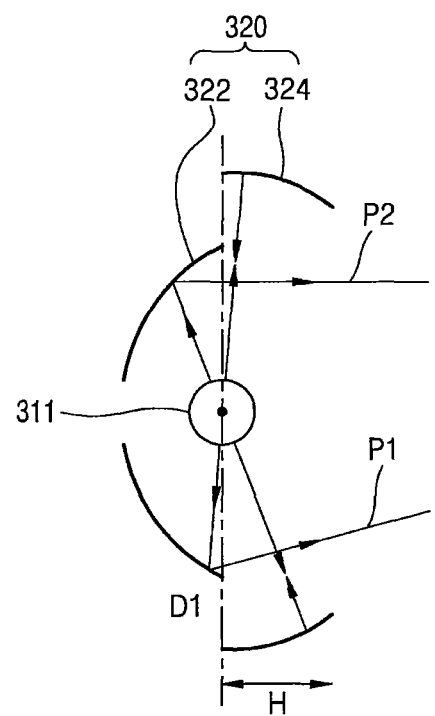

FIGS. 17 to 19 are diagrams illustrating the configuration and function of the reflection structure employed in the inspection apparatus 2000 of FIG. 16.

Referring to FIGS. 17 to 19, the reflection structure 320 may be configured such that the opening of the elliptical mirror 322 is surrounded by one opening of the spherical mirror 324. In FIG. 17, for easy understanding, the light source 310 is not illustrated. In FIGS. 18 and 19, only the chamber 311 is illustrated and the other parts of the light source 310 are not illustrated.

On the other hand, a left small opening of the elliptical mirror 322 may be formed or not formed according to a type of the light source 310. For example, in a case where the plasma light source illustrated in FIG. 1A is used, the left opening of the elliptical mirror 322 may not be formed. In addition, since the left opening of the elliptical mirror 322 does not contribute to light reflection, the left opening of the elliptical mirror 322 may be formed, regardless of the type of the light source 310.

As described above, the focus of the elliptical mirror 322 may be equal to the focus of the spherical mirror 324, and the chamber 311 may be disposed at that focus. More specifically, the chamber 311 may be disposed such that the converging point of the chamber 311 matches the focus of the elliptical mirror 322 and the spherical mirror 324. In addition, as illustrated, the elliptical mirror 322 is combined with the spherical mirror 324 such that the cross section of the opening of the elliptical mirror 322 is on the same plane as the cross section of the left opening of the spherical mirror 324. However, according to circumstances, the cross section of the opening of the elliptical mirror 322 is not on the same plane as the cross section of the left opening of the spherical mirror 324. For example, since the elliptical mirror 322 is combined while being slightly shifted to the right, the cross section of the opening of the elliptical mirror 322 may be disposed inside of the spherical mirror 324 and the periphery thereof may partially overlap the spherical mirror 324 accordingly.

On the other hand, by adjusting a height H of the spherical mirror 324, it is possible to adjust a total amount of light reflected by the elliptical mirror 322. For example, if the height H of the spherical mirror 324 is reduced, the amount of light reflected by the spherical mirror 324 may be reduced and the amount of light reflected again by the elliptical mirror 322 may also be reduced accordingly. On the contrary, if the height H of the spherical mirror 324 is increased, the amount of light reflected by the spherical mirror 324 may be increased and the amount of light reflected again by the elliptical mirror 322 may also be increased accordingly.

In addition, by adjusting the height H of the spherical mirror 324, it is possible to adjust the intensity of light reflected from the periphery of the elliptical mirror 322. In other words, the area of the re-reflection portion of the elliptical mirror 322 may be changed according to the height H of the spherical mirror 324. More specifically, as illustrated in FIG. 18, the light reflected by the spherical mirror 324 passes through the focus thereof, is directed toward the elliptical mirror 322, and is reflected toward the homogenizer 340 by the elliptical mirror 322. On the other hand, light P1 reflected from a portion of the spherical mirror 324, adjacent to the elliptical mirror 322, may be re-reflected from an outer periphery of the elliptical mirror 322, and light P2 reflected from the outer periphery of the spherical mirror 324, disposed farther from the elliptical mirror 322, may be re-reflected from a much inner side of the elliptical mirror 322. Therefore, as the height H of the spherical mirror 324 increases, the re-reflection region of the elliptical mirror 322 may be widened, and as the height H of the spherical mirror 324 decreases, the re-reflection region of the elliptical mirror 322 may be narrowed. In addition, since the re-reflected light is added, the intensity of light is increased in the re-reflected region of the elliptical mirror 322. As a result, it is possible to adjust the intensity of light in the periphery of the elliptical mirror 322 by adjusting the height H of the spherical mirror 324.

FIG. 20A is a simulation photograph of a light intensity distribution when only the elliptical mirror 322 is present in the inspection apparatus 2000 of FIG. 16, and FIG. 20B is a simulation photograph of a light intensity distribution when a reflection structure including the spherical mirror 324 is present in the inspection apparatus 2000 of FIG. 16. FIGS. 20A and 20B illustrate light intensity distributions on a pupil surface under the collimation lens 252 of the inspection apparatus 2000 of FIG. 16.

Referring to FIG. 20A, when only the elliptical mirror 322 is present, the intensity of light is gradually weaker as a distance increases from the central area to the outer peripheral area. However, as illustrated in FIG. 20B, when the reflection structure 320, including the spherical mirror 324, is present, the intensity of light is uniform as a whole. This is because the light returned by the reflection of the spherical mirror 324 is re-reflected at the outer periphery of the elliptical mirror 322 and the intensity of light is increased at the outer periphery of the elliptical mirror 322. Similar to the images of FIGS. 11A and 11B, in the images of FIGS. 20A and 20B, no light is present in dark areas in the central area and the outer peripheral area because light is blocked by the configurations of the light source 310 and the elliptical mirror 322.

FIGS. 21A and 21B are graphs when cutting the light intensity distributions of FIGS. 20A and 20B into an x slice and a y slice, respectively. The graphs of FIGS. 21A and 21B correspond to the images of FIGS. 20A and 20B, respectively.

Referring to FIG. 21A, when only the elliptical mirror 322 is present, the intensity of light is gradually weaker as a distance increases from the central area to the outer peripheral area. However, as illustrated in FIG. 21B, when the reflection structure 320, including the spherical mirror 324, is present, there is no great difference in the intensity of light between the central area and the outer peripheral area.

When numerically comparing the intensity of light in the graph of FIG. 21B with the intensity of light in the graph of FIG. 21A, the overall intensity of light in the graph of FIG. 21B is similar to the intensity of light in the central area in the graph of FIG. 21A. As a result, the inspection apparatus 2000 according to the present example embodiment increases the intensity of light in the outer peripheral area by employing the reflection structure 320, thus homogenizing the overall intensity of light. The central area Ac having low intensity of light corresponds to the central area where no light exists in the images of FIGS. 20A and 20B.

More specifically, in the intensity of light in the graph of FIG. 21B, the intensity of light is gradually reduced from the central area to the outer peripheral area, is increased in the middle area, and is then reduced again. The middle area where the intensity of light is increased may be an interface between a re-reflection area of the elliptical mirror 322 and an inner area where no re-reflection occurs. That is, in the inner area where no re-reflection occurs, the intensity of light is reduced toward the outer peripheral area as in the case where only the elliptical mirror 322 is present. In the re-reflection area, light added by the reflection of the spherical mirror 324 is re-reflected. Thus, the intensity of light may be increased as much. On the other hand, when the distribution of the light added by the reflection of the spherical mirror 324 is uniform, the intensity of light may be gradually weaker toward the outer peripheral area even in the re-reflection area of the elliptical mirror 322. However, the degree of weakening in the inner area or the re-reflection area may be very low, as compared with the case where only the elliptical mirror 322 is present.

Figure 22:
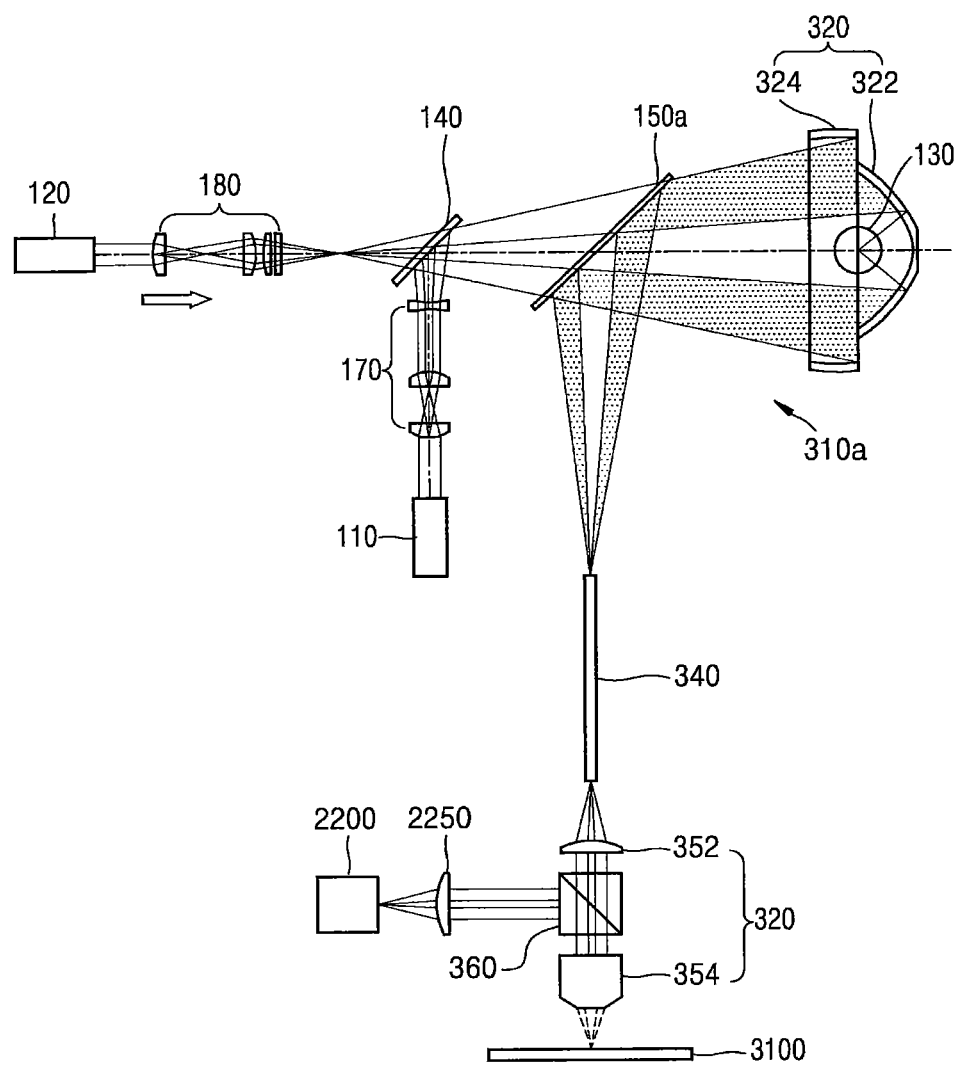
FIGS. 22 to 24 are schematic diagrams of inspection apparatuses including an illumination optical system, according to example embodiments of the inventive concept.
Figure 23:
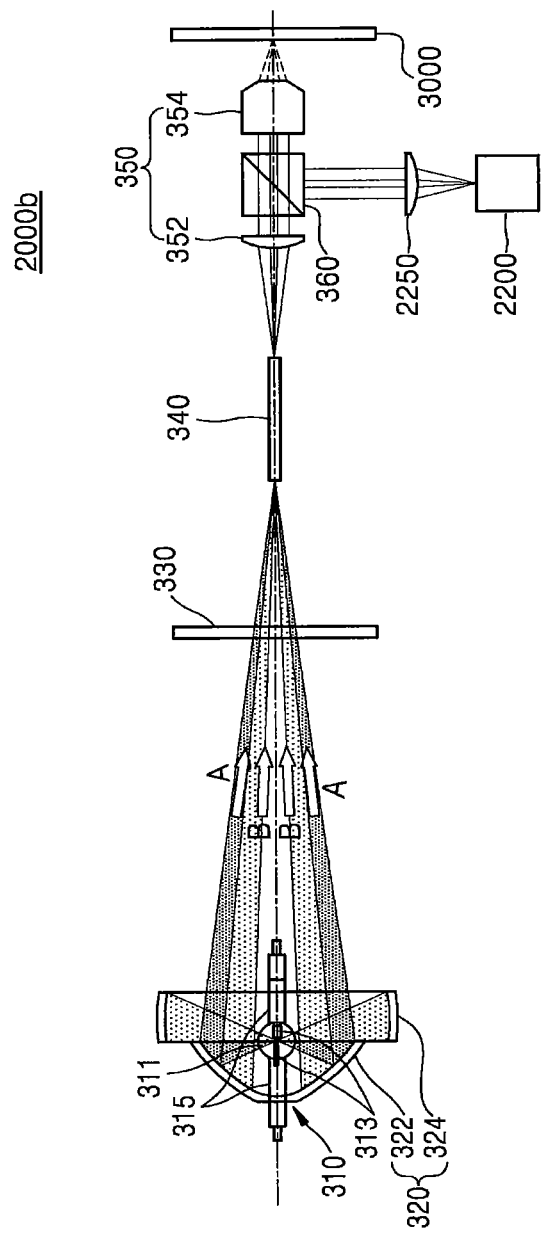
Figure 24:
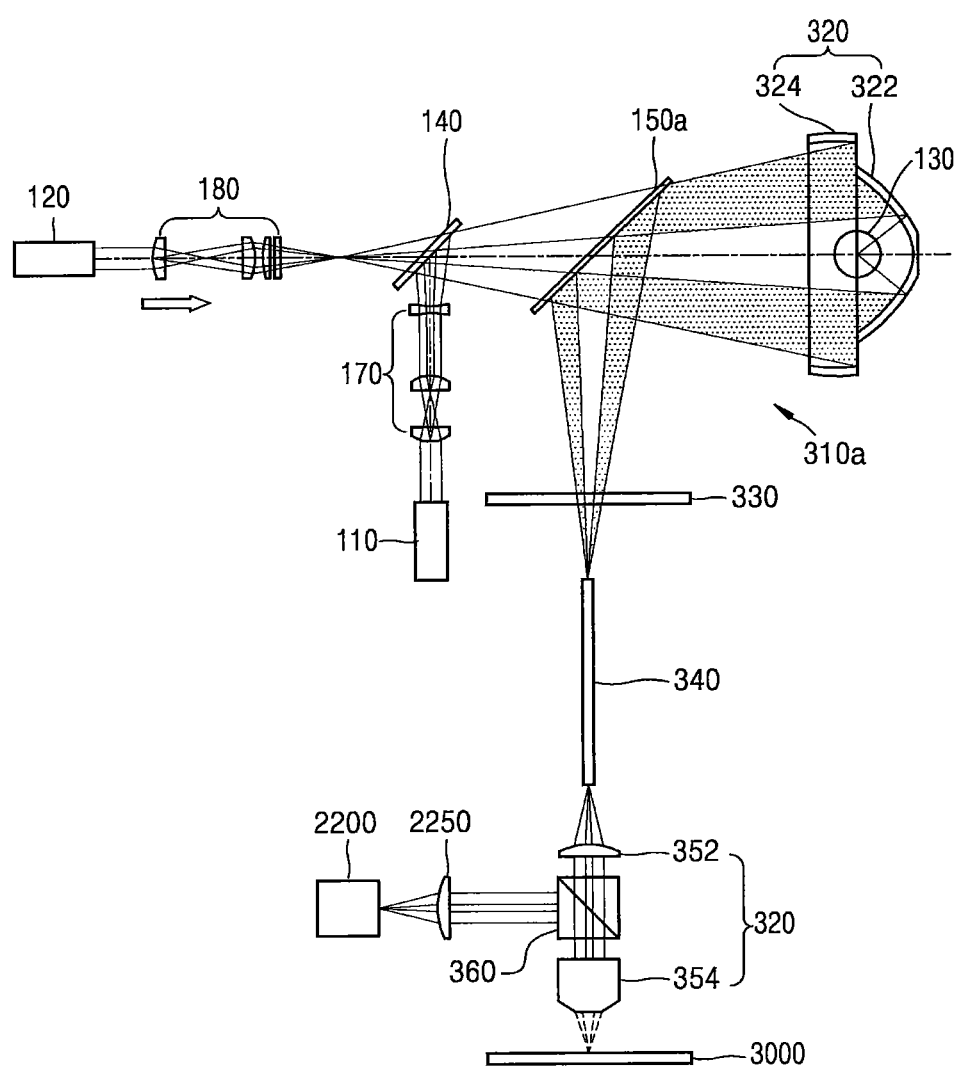

FIGS. 22 to 24 are schematic diagrams of inspection apparatuses 2000a, 2000b, and 2000c including an illumination optical system, according to example embodiments of the inventive concept.

Referring to FIG. 22, the inspection apparatus 2000a according to the present example embodiment differs from the inspection apparatus 2000 of FIG. 16 in terms of a type of a light source 310a. For example, the light source 310a may have the same configuration as the plasma light source 100 described with reference to FIGS. 1A and 1B, instead of a short arc discharge lamp. More specifically, the light source 310a may include a pulse laser generator 110, a CW laser generator 120, a chamber 130, a first dichroic mirror 140, a second dichroic mirror 150a, a first input optical system 170, a second input optical system 180, and a reflection structure 320.

A pulse laser beam (e.g., visible ray pulse laser beam) from the pulse laser generator 110 may be input to the chamber 130 and ignite plasma. A CW laser beam (e.g., IR CW laser beam) from the CW laser generator 120 may be input to the chamber 130, maintain the plasma in an ignited state, and increase the intensity of plasma. Plasma light (e.g., UV rays) discharged from the chamber 130 may be reflected toward the second dichroic mirror 150a by the reflection structure 320 and be reflected toward a homogenizer 340 by the second dichroic mirror 150a. Subsequent traveling processes of the output light may be substantially the same as those described above with reference to FIG. 16.

Since the inspection apparatus 2000a according to the present example embodiment includes the plasma light source 310a having an electrodeless chamber structure and employs the reflection structure 320, it is possible to simplify the light source structure, improve the brightness of light, and homogenize the light intensity distribution in terms of angle.

In the inspection apparatus 2000a according to the present example embodiment, the plasma light source 100 of FIGS. 1A and 1B is used as the light source 310a, but any one of the plasma light sources 100a to 100f of FIGS. 3 to 8 may be used instead of the light source 100 of FIG. 1A. In addition, in the inspection apparatus 2000a according to the present example embodiment, the light source 310a is not limited to the plasma light sources 100 and 100a to 100f of FIGS. 1A to 8. For example, in the inspection apparatus 2000a according to the example embodiment, examples of the light source 310a may include a plasma light source using various ignition sources, such as microwaves, UV rays, high-frequency waves, a flash lamp, or a pulse lamp. In addition, the light source 310a is not limited to a plasma light source and may be an LED light source or a laser light source.

In addition, in the inspection apparatus 2000a according to the present example embodiment, a beam splitter 360 may be disposed between a homogenizer 340 and the collimation lens 352 as in the inspection apparatus 1000b of FIG. 14. In addition, as in the inspection apparatus 1000a of FIG. 13, the inspection apparatus 2000a according to the present example embodiment may improve spatial arrangement utilization of elements by employing the mirror 270.

Referring to FIG. 23, the inspection apparatus 2000b according to the present example embodiment differs from the inspection apparatus 2000 of FIG. 16 in that an ND filter 330 is further included. For example, the inspection apparatus 2000b according to the present example embodiment may further include the ND filter 330 above the homogenizer 340. As such, since the inspection apparatus 2000b according to the present example embodiment further includes the ND filter 330, light intensity distribution may become more uniform in terms of angle.

For example, as can be seen from the graph of FIG. 21B, the intensity of light is gradually weaker as a distance increases from the re-reflection area of the elliptical mirror 322 and the inner area where no re-reflection occurs toward the outer peripheral area. Although the change in the intensity of light is slight, the light intensity distribution may be non-uniform in terms of angle. Therefore, by employing the ND filter 330, the inspection apparatus 2000b according to the present example embodiment may further homogenize the light intensity distribution in terms of angle.

In addition, in the inspection apparatus 2000b according to the present example embodiment, a beam splitter 360 may be disposed between a homogenizer 340 and a collimation lens 352, as in the inspection apparatus 1000b of FIG. 14. In addition, as in the inspection apparatus 1000a of FIG. 13, the inspection apparatus 2000b according to the present example embodiment may improve spatial arrangement utilization of elements by employing the mirror 270.

Referring to FIG. 24, the inspection apparatus 2000c according to the present example embodiment differs from the inspection apparatus 2000a of FIG. 22 in that an ND filter 330 is further included. Specifically, the inspection apparatus 2000c according to the present example embodiment may employ the structure of the plasma light source 100 of FIGS. 1A and 1B as the light source 310a and further include the ND filter 330 above a homogenizer 340.

Since the inspection apparatus 2000c according to the present example embodiment includes the plasma light source 310a having an electrodeless chamber structure and employs a reflection structure 320 and the ND filter 330, it is possible to simplify the light source structure, improve the brightness of light, and further homogenize the light intensity distribution in terms of angle.

In the inspection apparatus 2000c according to the present example embodiment, the light source 310a may be any one of the plasma light sources 100a to 100f of FIGS. 1A to 8. In the inspection apparatus 2000c according to the example embodiment, the light source 310a is not limited to the plasma light sources 100 and 100a to 100f of FIGS. 1A to 8 and may employ various plasma light sources as described above. In addition, the light source 310a is not limited to a plasma light source and may be an LED light source or a laser light source.

In the inspection apparatus 2000c according to the present example embodiment, the beam splitter 360 may be disposed between the homogenizer 340 and the collimation lens 352, as in the inspection apparatus 1000b of FIG. 14. In addition, as in the inspection apparatus 1000a of FIG. 13, the inspection apparatus 2000b according to the present example embodiment may improve spatial arrangement utilization of elements by employing the mirror 270.

While the inventive concept has been particularly shown and described with reference to example embodiments thereof, it will be understood that various changes in form and details may be made therein without departing from the spirit and scope of the following claims.

What is claimed is:

1. A plasma light source comprising:
a pulse laser generator configured to generate a pulse laser beam;
a continuous wave (CW) laser generator configured to generate an infrared ray (IR) CW laser beam;
a first dichroic mirror configured to selectively transmit or reflect the pulse laser beam and to selectively reflect or transmit the IR CW laser beam;
a chamber configured to receive the pulse laser beam to ignite plasma and the IR CW laser beam to maintain the plasma in an ignited state, and to discharge plasma light generated by the plasma; and
a second dichroic mirror configured to transmit the pulse laser beam and the IR CW laser beam and reflect the plasma light, wherein the pulse laser beam is a ring-shaped beam and is input to the first dichroic mirror.

2. The plasma light source of claim 1, wherein the chamber has no electrodes therein.

3. The plasma light source of claim 1, wherein the chamber is surrounded by an elliptical mirror and is disposed at a focus of the elliptical mirror, and
the pulse laser beam and the IR CW laser beam are concentrated on the chamber by the elliptical mirror.

4. The plasma light source of claim 1, wherein the first dichroic mirror and the second dichroic mirror are disposed on a same axis to selectively reflect or transmit light according to a wavelength, so that input light beams incident on the chamber are synthesized and an output light beam from the chamber is separated from the input light beams.

5. The plasma light source of claim 1, wherein the pulse laser beam is input to the chamber by reflection of the first dichroic mirror and transmission of the second dichroic mirror, and
the IR CW laser beam passes through the first dichroic mirror and the second dichroic mirror and is input to the chamber.

6. A plasma light source comprising:
a pulse laser generator configured to generate a pulse laser beam;
a continuous wave (CW) laser generator configured to generate an infrared ray (IR) CW laser beam;
a first dichroic mirror configured to selectively transmit or reflect the pulse laser beam and to selectively reflect or transmit the IR CW laser beam;
a chamber configured to receive the pulse laser beam to ignite plasma and the IR CW laser beam to maintain the plasma in an ignited state, and to discharge plasma light generated by the plasma; and
a second dichroic mirror configured to transmit the pulse laser beam and the IR CW laser beam and reflect the plasma light,
wherein the pulse laser beam is input to the chamber by reflection of the first dichroic mirror and transmission of the second dichroic mirror,
the IR CW laser beam passes through the first dichroic mirror and the second dichroic mirror and is input to the chamber,
a concave lens is disposed between the pulse laser generator and the first dichroic mirror, and
a cylindrical lens is disposed between the CW laser generator and the first dichroic mirror.

7. An inspection apparatus comprising:
a plasma light source including:
a first dichroic mirror configured to transmit or reflect a pulse laser beam and reflect or transmit an infrared ray (IR) continuous wave (CW) laser beam;
a chamber configured to receive the pulse laser beam to ignite plasma and the IR CW laser beam to maintain the plasma in an ignited state, and discharge plasma light generated by the plasma; and
a second dichroic mirror configured to transmit or reflect the pulse laser beam and the IR CW laser beam and reflect the plasma light, wherein the pulse laser beam is a ring-shaped beam and is input to the first dichroic mirror;
a first optical system configured to transfer the plasma light to an inspection object; and
a second optical system comprising an optical detector configured to detect light reflected from the inspection object.

8. The inspection apparatus of claim 7, wherein the chamber is surrounded by an elliptical mirror and is disposed at a focus of the elliptical mirror,
the pulse laser beam and the IR CW laser beam are concentrated on the chamber by the elliptical mirror, and
the first dichroic mirror and the second dichroic mirror reflect or transmit light according to a wavelength, so that input light beams incident on the chamber are synthesized and an output light beam from the chamber is separated from the input light beams.

9. The inspection apparatus of claim 7, wherein the chamber has no electrodes therein.

10. The inspection apparatus of claim 9, further comprising a uniformizing device including a neutral density (ND) filter disposed between the plasma light source and the first optical system and configured to gradually reduce a transmittance of the plasma light toward a central area of a cross section perpendicular to a traveling direction of the plasma light.

11. The inspection apparatus of claim 10, wherein the uniformizing device is a reflection structure that includes a combination of an elliptical mirror and a spherical mirror and reflects the plasma light in one direction,
the elliptical mirror has a structure that is opened in a direction of a homogenizer, the spherical mirror is opened in a first direction and a second direction, the first direction being directed toward the elliptical mirror and the second direction being directed toward the homogenizer, and
the reflection structure is configured such that an opened portion of the spherical mirror in the first direction is coupled to an opened portion of the elliptical mirror.

12. The inspection apparatus of claim 11, wherein the spherical mirror is configured to reflect the plasma light, which is not reflected by the elliptical mirror, toward the elliptical mirror, and
the spherical mirror is configured to homogenize an intensity of the plasma light in the central area and the intensity of the plasma light in an outer peripheral area on a cross section perpendicular to the traveling direction of the plasma light.

13. The inspection apparatus of claim 7, further comprising:
a uniformizing device including a reflection structure that includes a combination of an elliptical mirror and a spherical mirror and reflects the plasma light in one direction; and
a neutral density (ND) filter disposed between the reflection structure and the first optical system and configured to gradually reduce the transmittance of the plasma light toward a central area of a cross section perpendicular to a traveling direction of the plasma light.

14. The inspection apparatus of claim 7, wherein the first optical system includes:
- a collimation lens configured to collimate light output from a homogenizer into parallel light; and
- an objective lens configured to irradiate the parallel light on the inspection object and receive light reflected from the inspection object, and
- the inspection apparatus further comprises a beam splitter disposed between the collimation lens and the objective lens or between the homogenizer and the collimation lens to split the light irradiated on the inspection object and the light reflected from the inspection object.

* * * * *